(12) United States Patent
Buettelmann et al.

(10) Patent No.: US 7,432,256 B2
(45) Date of Patent: Oct. 7, 2008

(54) SUBSTITUED IMIDAZO [1,5-A][1,2,4]TRIAZOLO[1,5-D][1,4] BENZODIAZEPINE DERIVATIVES

(75) Inventors: Bernd Buettelmann, Schopfheim (DE); Henner Knust, Rheinfelden (DE); Andrew William Thomas, Birsfelden (CH)

(73) Assignee: Hoffman-La Roche Inc., Nutley, NJ (US)

( * ) Notice: Subject to any disclaimer, the term of this patent is extended or adjusted under 35 U.S.C. 154(b) by 482 days.

(21) Appl. No.: 11/297,691

(22) Filed: Dec. 8, 2005

(65) Prior Publication Data
US 2006/0128691 A1   Jun. 15, 2006

(30) Foreign Application Priority Data
Dec. 14, 2004  (EP) ................... 04106556

(51) Int. Cl.
A61P 25/28 (2006.01)
A61K 31/551 (2006.01)
C07D 487/12 (2006.01)

(52) U.S. Cl. ........................ 514/219; 540/555
(58) Field of Classification Search ............... 514/219; 540/555
See application file for complete search history.

(56) References Cited

U.S. PATENT DOCUMENTS

| | | |
|---|---|---|
| 4,316,839 A | 2/1982 | Gerecke et al. |
| 4,772,599 A | 9/1988 | Wätjen |
| 4,775,671 A | 10/1988 | Hunkeler et al. |
| 4,897,392 A | 1/1990 | Tegeler et al. |
| 5,387,585 A | 2/1995 | Borer et al. |

FOREIGN PATENT DOCUMENTS

| | | |
|---|---|---|
| EP | 0 027 214 | 4/1981 |
| EP | 0 150 040 | 1/1985 |
| EP | 0 519 307 | 10/1992 |
| WO | WO 02/40487 | 5/2002 |

OTHER PUBLICATIONS

McNamara, et al., Psychobiology (1993), vol. 21(2) pp. 101-108.
Gerecke, et al., Heterocycles (1994), vol. 39, No. 2, pp. 693-721.
Breuer, Tetrahedron Letters (1976) No. 23, pp. 1935-1938.
Möhler et al., Nature (1981) vol. 294 pp. 763-765.
Möhler et al., Journal of Neurochemistry (1981), vol. 37(3), pp. 714-722.
Chemical Abstract 204054p, vol. 90, 1979 p. 624.
Chemical Abstract 37799s, vol. 108, 1988 p. 635.
Drug Evaluations, 6th Ed. (1986), American Medical Association, pp. 160-162.
Thompson et al. The New England Journal of Medicine (1990), vol. 323(7) pp. 445-448.
Rennie, Scientific American (1992) pp. 20 & 26.
Berkow et al., eds., The Merck Manual of Diagnosis & Therapy, 15th Ed. (1987) pp. 839-840.
Wyngaarden, et al., eds., Cecil Textbook of Medicine, 19th Ed. (1992), pp. 2075-2079.

Primary Examiner—Brenda L Coleman
(74) Attorney, Agent, or Firm—George W. Johnston; Patricia S. Rocha-Tramaloni; Kimberly J. Prior

(57) ABSTRACT

The present invention is concerned with substituted imidazo [1,5-a][1,2,4]triazolo[1,5-d][1,4]benzodiazepine derivatives of the formula I

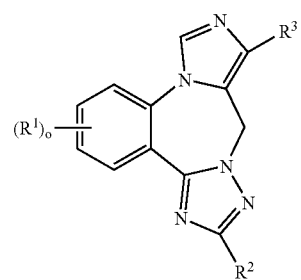

wherein
$R^1$ is hydrogen, halogen, lower alkyl, lower alkyl substituted by halogen, lower alkoxy, lower alkoxy substituted by halogen, nitro, cycloalkyl, $-O(CH_2)_m O(CH_2)_m OH$ or $-C\equiv C-R'$;
$R^2$ is hydrogen or methyl;
$R^3$ is lower alkyl, lower alkyl substituted by halogen, lower alkenyl, lower alkenyl substituted by halogen, lower alkynyl, $-(CH_2)_n$-cycloalkyl, $-(CR'R'')_m-CH_3$, phenyl that is unsubstituted or substituted by halogen, pyridinyl or thienyl each of which is unsubstituted or substituted by lower alkyl, $-(CH_2)_n-NH$-cycloalkyl, lower alkenyl-cycloalkyl, lower alkynyl-$(CR'R'')_m OH$, or lower alkynyl-phenyl wherein the phenyl ring is unsubstituited or substituted by halogen, $CF_3$, lower alkyl or lower alkoxy;
R' is hydrogen or lower alkyl;
R" is hydrogen, hydroxy or lower alkyl;
n is 0, 1 or 2;
m is 1, 2 or 3; and
o is 1 or 2;
and pharmaceutically acceptable acid addition salts thereof. This class of compounds have high affinity and selectivity for GABA A α5 receptor binding sites. Thus, the invention also relates to methods of enhancing cognition and treating cognitive disorders like Alzheimer's disease.

24 Claims, No Drawings

SUBSTITUED IMIDAZO [1,5-A][1,2,4]TRIAZOLO[1,5-D][1,4] BENZODIAZEPINE DERIVATIVES

PRIORITY TO RELATED APPLICATIONS

This application claims the benefit of European Application No. 04106556.6 filed Dec. 14, 2004, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in *Psychobiology*, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY OF THE INVENTION

The present invention provides substituted imidazo[1,5-a] [1,2,4]triazolo[1,5-d][1,4]benzodiazepine derivatives of formula I

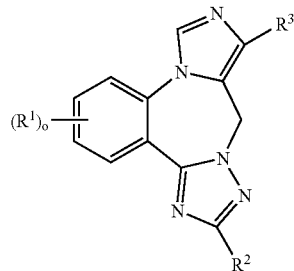

I wherein $R^1$ is hydrogen, halogen, lower alkyl, lower alkyl substituted by halogen, lower alkoxy, lower alkoxy substituted by halogen, nitro, cycloalkyl, —O(CH$_2$)$_m$O(CH$_2$)$_m$OH or —C≡C—R';

$R^2$ is hydrogen or methyl;

$R^3$ is lower alkyl, lower alkyl substituted by halogen, lower alkenyl, lower alkenyl substituted by halogen, lower alkynyl, —(CH$_2$)$_n$-cycloalkyl, —(CR'R")$_m$—CH$_3$, phenyl that is unsubstituted or substituted by halogen, pyridinyl or thienyl each of which is unsubstituted or substituted by lower alkyl, —(CH$_2$)$_n$—NH-cycloalkyl, lower alkenyl-cycloalkyl, lower alkynyl-(CR'R")$_m$OH, or lower alkynyl-phenyl wherein the phenyl ring is unsubstituited or substituted by halogen, CF$_3$, lower alkyl or lower alkoxy;

R' is hydrogen or lower alkyl;

R" is hydrogen, hydroxy or lower alkyl;

n is 0, 1 or 2;

m is 1, 2 or 3; and o is 1 or 2;

and pharmaceutically acceptable acid addition salts thereof.

The present invention also provides pharmaceutical compositions containing a therapeutically effective amount of a compound of the invention and methods for the preparation of such compounds and compositions.

Compounds of the invention have a high affinity and selectivity for GABA A α5 receptor binding sites and, therefore, the invention also provides methods of enhancing cognition and methods for the treatment of cognitive disorders like Alzheimer's disease. The most preferred indication in accordance with the present invention is Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain alkyl group containing from 1-7, preferably from 1-4, carbon atoms, for example, methyl, ethyl, propyl, isopropyl, n-butyl, i-butyl, t-butyl and the like.

As used herein, the term "lower alkyl substituted by halogen" denotes a straight- or branched-chain alkyl group containing from 1-7, preferably from 1-4, carbon atoms, for example, methyl, ethyl, propyl, isopropyl, n-butyl, i-butyl, t-butyl and the like, wherein at least one hydrogen atom is replaced by a halogen atom.

As used herein, the term "lower alkoxy" denotes a straight- or branched-chain alkyl group containing from 1-7, preferably from 1-4, carbon atoms, for example, methyl, ethyl, propyl, isopropyl, n-butyl, i-butyl, t-butyl and the like, as described above, which is attached via an oxygen group.

As used herein, the term "lower alkoxy substituted by halogen" denotes a straight- or branched-chain alkyl group containing from 1-7, preferably from 1-4, carbon atoms, for example, methyl, ethyl, propyl, isopropyl, n-butyl, i-butyl, t-butyl and the like, as described above which is attached via an oxygen group, wherein at least one hydrogen atom is replaced by a halogen atom.

The term "lower alkenyl" denotes a straight- or branched-chain carbon group containing from 2-7, preferably from 2-4, carbon atoms, wherein at least one bond is a double bond.

The term "lower alkenyl substituted by halogen" denotes a straight- or branched-chain carbon group containing from 2-7, preferably from 2-4, carbon atoms, wherein at least one bond is a double bond and wherein at least one hydrogen atom is replaced by a halogen atom.

The term "lower alkynyl" denotes a straight- or branched-chain carbon group containing from 2-7, preferably from 2-4, carbon atoms, wherein at least one bond is a triple bond.

The term "halogen" denotes chlorine, iodine, fluorine and bromine.

The term "cycloalkyl" denotes a cyclic alkyl ring, having from 3 to 7 carbon ring atoms, for example, cyclopropyl, cyclopentyl or cyclohexyl.

The term "pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

The term "therapeutically effective amount" means an amount that is effective to prevent, alleviate or ameliorate symptoms of disease or prolong the survival of the subject being treated.

The present invention provides substituted imidazo[1,5-a][1,2,4]triazolo[1,5-d][1,4]benzodiazepine derivatives of formula I

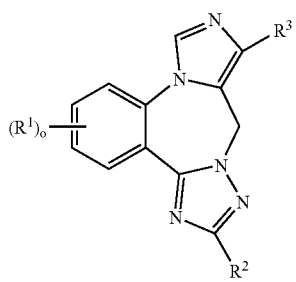

I wherein
R$^1$ is hydrogen, halogen, lower alkyl, lower alkyl substituted by halogen, lower alkoxy, lower alkoxy substituted by halogen, nitro, cycloalkyl, —O(CH$_2$)$_m$O(CH$_2$)$_m$OH or —C≡C—R';
R$^2$ is hydrogen or methyl;
R$^3$ is lower alkyl, lower alkyl substituted by halogen, lower alkenyl, lower alkenyl substituted by halogen, lower alkynyl, —(CH$_2$)$_n$-cycloalkyl, —(CR'R")$_m$—CH$_3$, phenyl that is unsubstituted or substituted by halogen, pyridinyl or thienyl each of which is unsubstituted or substituted by lower alkyl, —(CH$_2$)$_n$—NH-cycloalkyl, lower alkenyl-cycloalkyl, lower alkynyl-(CR'R")$_m$OH, or lower alkynyl-phenyl wherein the phenyl ring is unsubstituited or substituted by halogen, CF$_3$, lower alkyl or lower alkoxy;
R' is hydrogen or lower alkyl;
R" is hydrogen, hydroxy or lower alkyl;
n is 0, 1 or 2;
m is 1, 2 or 3; and
o is 1 or 2;

and pharmaceutically acceptable acid addition salts thereof.

Exemplary preferred are compounds, which have a binding activity (Ki) of lower than 5 nM and are selective for GABA A α5 subunits and are relatively free of activity at GABA A α1, α2 and α3 receptor binding sites.

Preferred compounds of formula I are those, in which R$^3$ is lower alkyl, for example the following compounds:
10-methyl-9H-imidazo[1,5-a][1,2,4]triazolo[1,5-d][1,4]benzodiazepine,
3-fluoro-10-methyl-9H-imidazo[1,5-a][1,2,4]triazolo[1,5-d][1,4]benzodiazepine,
3-chloro-10-methyl-9H-imidazo[1,5-a][1,2,4]triazolo[1,5-d][1,4]benzodiazepine,
10-ethyl-3-fluoro-9H-imidazo[1,5-a][1,2,4]triazolo[1,5-d][1,4]benzodiazepine,
3-chloro-10-ethyl-9H-imidazo[1,5-a][1,2,4]triazolo[1,5-d][1,4]benzodiazepine,
10-ethyl-3-methoxy-9H-imidazo[1,5-a][1,2,4]triazolo[1,5-d][1,4]benzodiazepine,
3-chloro-10-propyl-9H-imidazo[1,5-a][1,2,4]triazolo[1,5-d][1,4]benzodiazepine,
3-bromo-10-propyl-9H-imidazo[1,5-a][1,2,4]triazolo[1,5-d][1,4]benzodiazepine,
3-iodo-10-methyl-9H-imidazo[1,5-a][1,2,4]triazolo[1,5-d][1,4]benzodiazepine,
4-chloro-3-fluoro-10-methyl-9H-imidazo[1,5-a][1,2,4]triazolo[1,5-d][1,4]benzodiazepine,
4-fluoro-10-methyl-9H-imidazo[1,5-a][1,2,4]triazolo[1,5-d][1,4]benzodiazepine and
4-chloro-10-methyl-9H-imidazo[1,5-a][1,2,4]triazolo[1,5-d][1,4]benzodiazepine.

Further preferred are compounds, wherein R$^3$ is —(CH$_2$)$_n$-cycloalkyl, an example is the compound
3-chloro-10-cyclopropylmethyl-9H-imidazo[1,5-a][1,2,4]triazolo[1,5-d][1,4]benzodiazepine.

Preferred compounds of formula I are further those, in which R$^3$ is lower alkenyl, for example the following compounds
10-vinyl-9H-imidazo[1,5-a][1,2,4]triazolo[1,5-d][1,4]benzodiazepine,
3-fluoro-10-vinyl-9H-imidazo[1,5-a][1,2,4]triazolo[1,5-d][1,4]benzodiazepine,
3-chloro-10-vinyl-9H-imidazo[1,5-a][1,2,4]triazolo[1,5-d][1,4]benzodiazepine,
3-chloro-10-(E)-propenyl-9H-imidazo[1,5-a][1,2,4]triazolo[1,5-d][1,4]benzodiazepine and
3-chloro-10-(Z)-propenyl-9H-imidazo[1,5-a][1,2,4]triazolo[1,5-d][1,4]benzodiazepine.

Further preferred are compounds, wherein R$^3$ is lower alkenyl-cycloalkyl, for example the following compounds
3-chloro-10-((E)-2-cyclopropyl-vinyl)-9H-imidazo[1,5-a][1,2,4]triazolo[1,5-d][1,4]benzodiazepine and
3-chloro-10-((Z)-2-cyclopropyl-vinyl)-9H-imidazo[1,5-a][1,2,4]triazolo[1,5-d][1,4]benzodiazepine.

Further preferred are compounds, wherein R$^3$ is lower alkynyl, for example the following compounds
10-ethynyl-3-fluoro-9H-imidazo[1,5-a][1,2,4]triazolo[1,5-d][1,4]benzodiazepine,
3-chloro-10-ethynyl-9H-imidazo[1,5-a][1,2,4]triazolo[1,5-d][1,4]benzodiazepine and
3-bromo-10-ethynyl-9H-imidazo[1,5-a][1,2,4]triazolo[1,5-d][1,4]benzodiazepine.

Further preferred are compounds, wherein R$^3$ is optionally substituted lower alkynyl-phenyl, for example the following compounds
3-fluoro-10-phenylethynyl-9H-imidazo[1,5-a][1,2,4]triazolo[1,5-d][1,4]benzodiazepine,
3-chloro-10-phenylethynyl-9H-imidazo[1,5-a][1,2,4]triazolo[1,5-d][1,4]benzodiazepine,
3-fluoro-10-(3-fluoro-phenylethynyl)-9H-imidazo[1,5-a][1,2,4]triazolo[1,5-d][1,4]benzodiazepine,
3-fluoro-10-(3-chloro-phenylethynyl)-9H-imidazo[1,5-a][1,2,4]triazolo[1,5-d][1,4]benzodiazepine,
3-fluoro-10-(3-trifluoromethyl-phenylethynyl)-9H-imidazo[1,5-a][1,2,4]triazolo[1,5-d][1,4]benzodiazepine,
3-fluoro-10-(3-methoxy-phenylethynyl)-9H-imidazo[1,5-a][1,2,4]triazolo[1,5-d][1,4]benzodiazepine,
3-fluoro-10-(3-methyl-phenylethynyl)-9H-imidazo[1,5-a][1,2,4]triazolo[1,5-d][1,4]benzodiazepine and
3-fluoro-10-(3-isopropyl-phenylethynyl)-9H-imidazo[1,5-a][1,2,4]triazolo[1,5-d][1,4]benzodiazepine.

Further preferred are compounds, wherein R$^3$ is optionally substituted lower alkynyl-(CR'R")$_m$OH, for example the following compound
3-chloro-10-(3-hydroxy-3-methyl-but-1-ynyl)-9H-imidazo[1,5-a][1,2,4]triazolo[1,5-d][1,4]benzodiazepine.

Further preferred are compounds of formula I, wherein $R^3$ in lower alkenyl substituted by halogen or is lower alkyl substituted by halogen, for example the following compounds
10-(2,2-difluoro-vinyl)-9H-imidazo[1,5-a][1,2,4]triazolo[1,5-d][1,4]benzodiazepine and
10-(2,2-difluoro-ethyl)-9H-imidazo[1,5-a][1,2,4]triazolo[1,5-d][1,4]benzodiazepine.

Further preferred compounds are those in which $R^1$ is lower alkyl, lower alkyl substituted by halogen, or cycloalkyl.

Further preferred compounds are those in which $R^1$ is lower alkoxy, lower alkoxy substituted by halogen, or $-O(CH_2)_mO(CH_2)_mOH$.

Further preferred compounds are those in which $R^1$ is hydrogen, halogen, nitro, or $-C\equiv C-R'$.

Further preferred compounds are those in which $R^2$ is hydrogen.

Further preferred compounds are those in which $R^2$ is methyl.

The present compounds of formula I and their pharmaceutically acceptable salts can be prepared by methods known in the art, for example, by processes described below, which processes comprise a) reacting a compound of formula

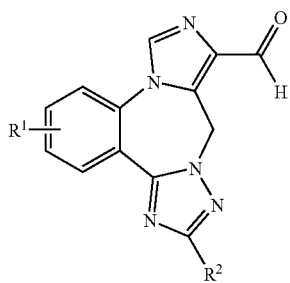

II with hydrazine and potassium hydroxide by Wolf-Kishner-reduction to produce a compound of formula

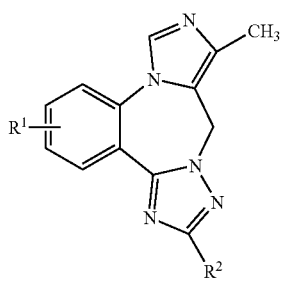

I-1 wherein $R^1$ and $R^2$ are as described above, or b) reacting a compound of formula

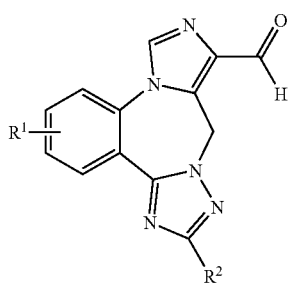

II with an amine of formula $H_2N$-cycloalkyl, in the presence of $NaBH_4$ to produce a compound of formula

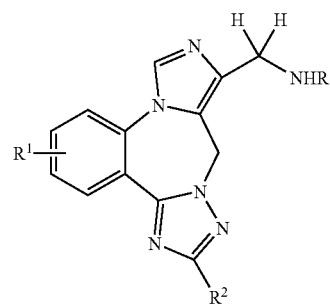

I-2

R is cycloalkyl wherein $R^1$ and $R^2$ are as described above, or c) reacting a compound of formula

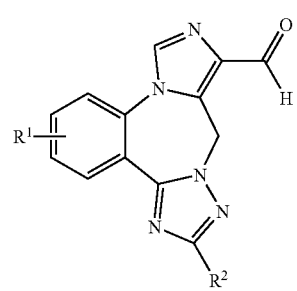

II with a compound of formula $R^4R^5=PPh_3$, wherein $R^4$ and $R^5$ are independently hydrogen, halogen, lower alkyl or cycloalkyl, to produce a compound of formula

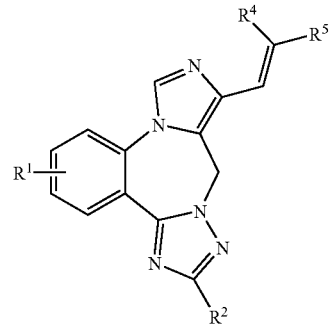

I-3 wherein $R^1$ and $R^2$ are as described above, or d) hydrogenating a compound of formula

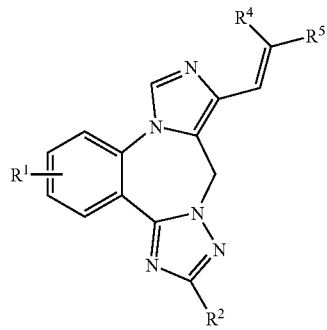

in the presence of Pd/C to produce a compound of formula

I-3

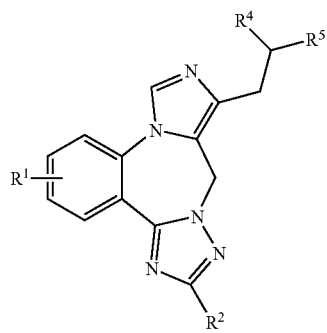

I-4 wherein $R^4$ and $R^5$ are independently hydrogen, halogen, lower alkyl or cycloalkyl and $R^1$ and $R^2$ are as described above, or e) reacting a compound of formula

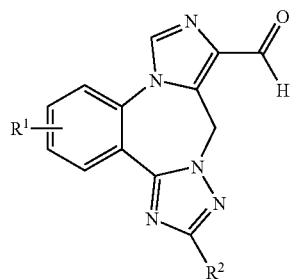

II with a compound of formula

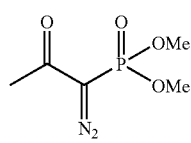

to produce a compound of formula

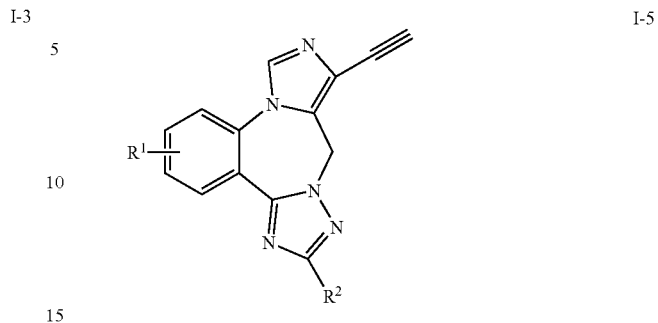

I-5 wherein $R^1$ and $R^2$ are as described above, or f) reacting a compound of formula

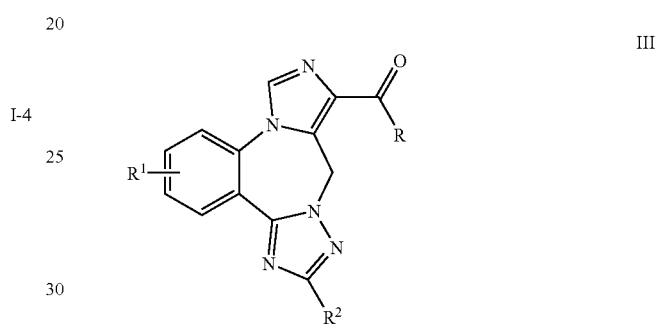

III with hydrazine and potassium hydroxide by Wolf-Kishner-reduction to produce a compound of formula

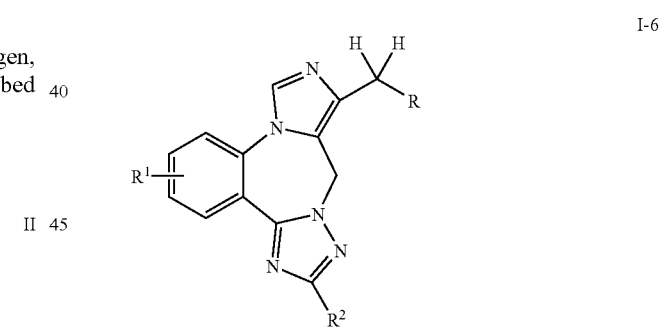

I-6 wherein $R^1$ and $R^2$ are as described above and R is lower alkyl, or g) reducing a compound of formula

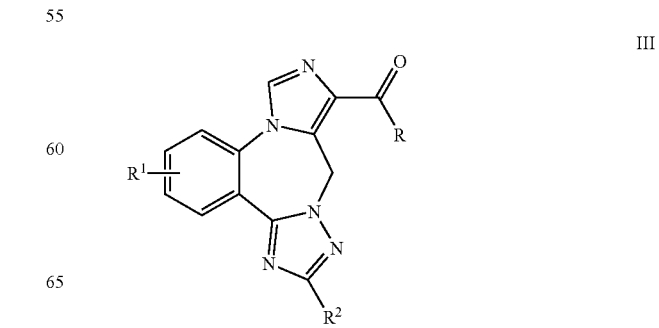

III with a reducing reagent, such as sodium borohydride, to a produce compound of formula

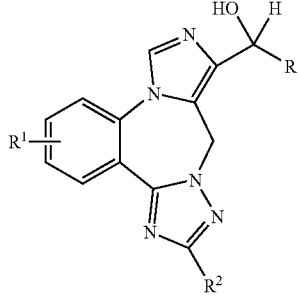

I-7 wherein R¹ and R² are as described above and R is lower alkyl, or h) reacting a compound of formula

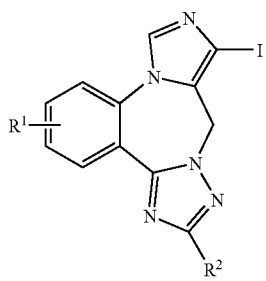

IV with a compound of formula

X—Ar wherein X is —B(OH)$_2$, —ZnBr, —ZnCl or —Sn(alkyl)$_3$ and Ar is unsubstituted or substituted phenyl or unsubstituted or substituted pyridyl, under palladium(0) catalysis to produce a compound of formula

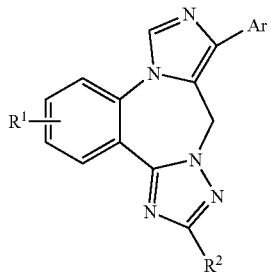

I-8 wherein R¹ and R² are as described above, or i) reacting a compound of formula

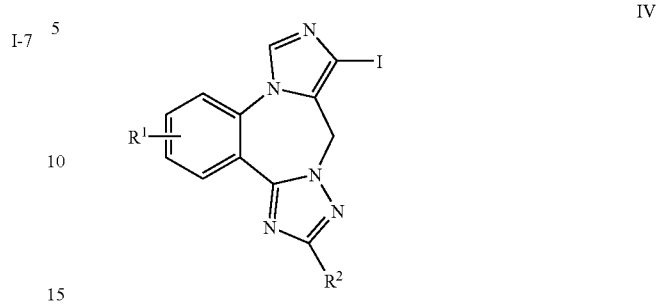

IV with a compound of formula

H≡≡Ar wherein Ar is unsubstituted or substituted phenyl or unsubstituted or substituted pyridyl, under palladium(0) or copper(I) catalysis to produce a compound of formula

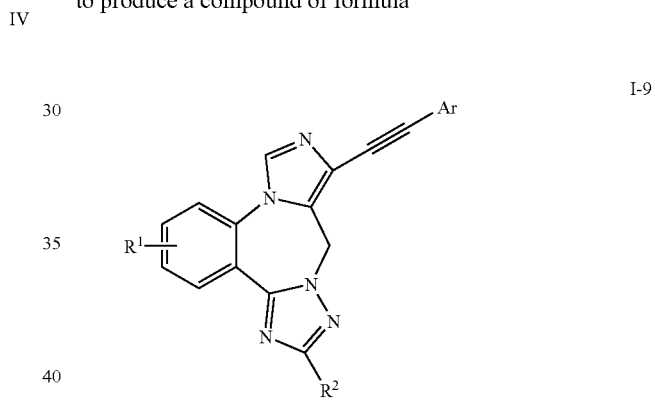

I-9 wherein R¹ and R² are as described above, or j) reacting a compound of formula

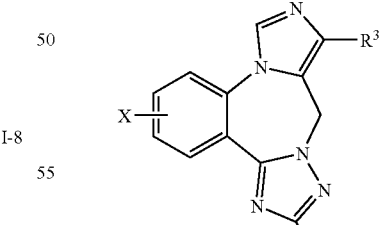

I-10 wherein X is halogen, preferably bromo, with a compound of formula

R¹—ZnCl or R¹—Sn(alkyl)$_3$ wherein R¹ is lower alkyl, cycloalkyl or —C≡C—R' under palladium(0) catalysis
to produce a compound of formula

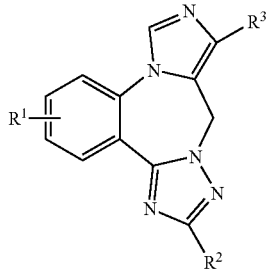
I-11 wherein R² and R³ are as described above and R¹ is lower alkyl, cycloalkyl or —C≡C—R', or k) reacting a compound of formula

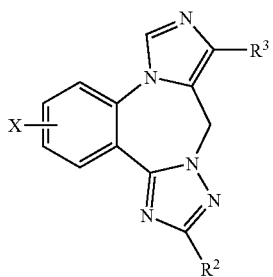
I-10 wherein X is halogen, preferably fluoro,
with a compound of formula

R¹'—ONa wherein R¹' is lower alkyl or —(CH₂)$_m$O(CH₂)$_m$OH to produce a compound of formula

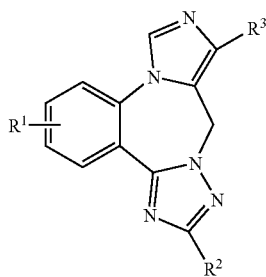
I-12 wherein R² and R³ are as described above and R¹ is lower alkoxy or —O(CH₂)$_m$O(CH₂)$_m$OH or l) reacting a compound of formula

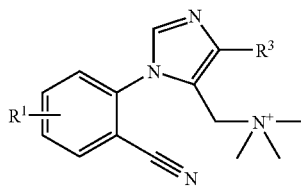
V with a compound of formula

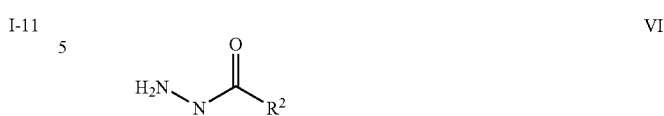
VI to produce a compound of formula

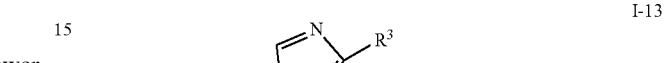
I-13 wherein R¹ and R² are as described above and R³ is lower alkyl, and, if desired, converting a compound of formula I into a pharmaceutically acceptable salt.

The following schemes (schemes 1-11) describe the processes for preparation of compounds of formula I in more detail. The starting materials are known compounds or can be prepared according to methods known in the art.

Scheme 1

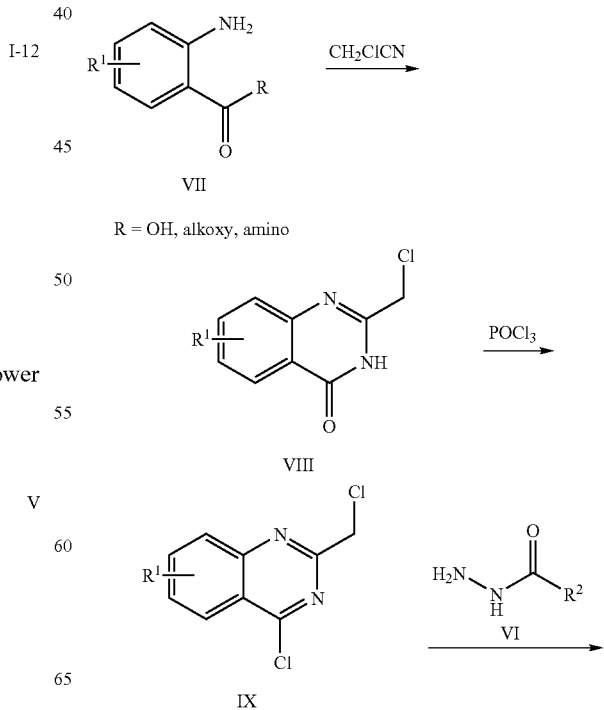

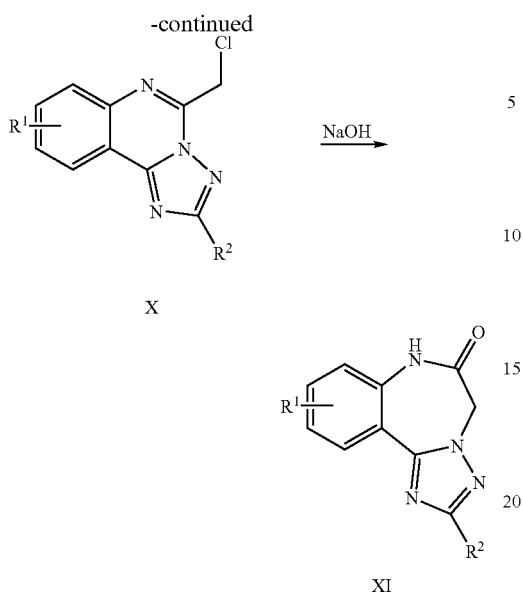

wherein $R^1$ and $R^2$ are as described above.

In accordance with scheme 1, a corresponding intermediate compound of formula XI is known (EP 519 307) and can be prepared by methods, known in the art, for example in the following way.

A corresponding compound of formula VII, an $R^1$-substituted 2-aminobenzoic acid derivative, and chloroacetonitrile is dissolved in dioxane, and a weak stream of dry HCl is introduced at 5° C. to 15° C. for a period of several hours. After addition of further chloroacetonitrile the mixture is stirred at ambient temperature for several hours. The obtained compound of formula VIII is purified in conventional manner and dissolved in chloroform in the presence of N,N-dimethyl-p-toluidine. Phosphorous oxide chloride is added, and the solution heated. The obtained compound of formula IX is purified by known methods and heated with a compound of formula VI, an acylhydrazide, in toluene for several hours, affording a compound of formula X, for example the compound 5-chloromethyl-9-fluoro-1,2,4-triazolo[4,3-c]quinazoline. Finally, a compound of XI is obtained by dissolving a compound of formula X in dioxane and treating with aqueous sodium hydroxide in such manner that the reaction temperature is between 10° C. to 15° C. Conventional workup and purification affords a corresponding intermediate of formula XI, for example 10-fluoro-5H-[1,2,4]triazolo[1,5-d][1,4]benzodiazepin-6(7H)-one.

Scheme 2

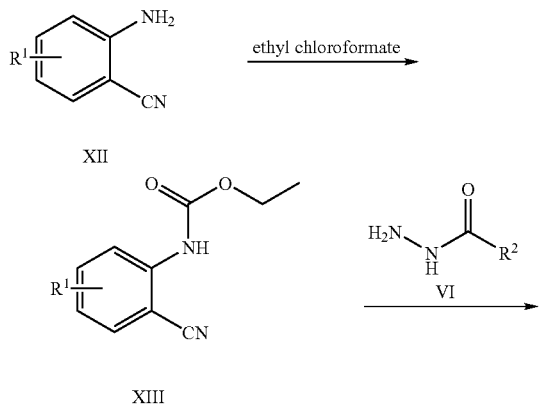

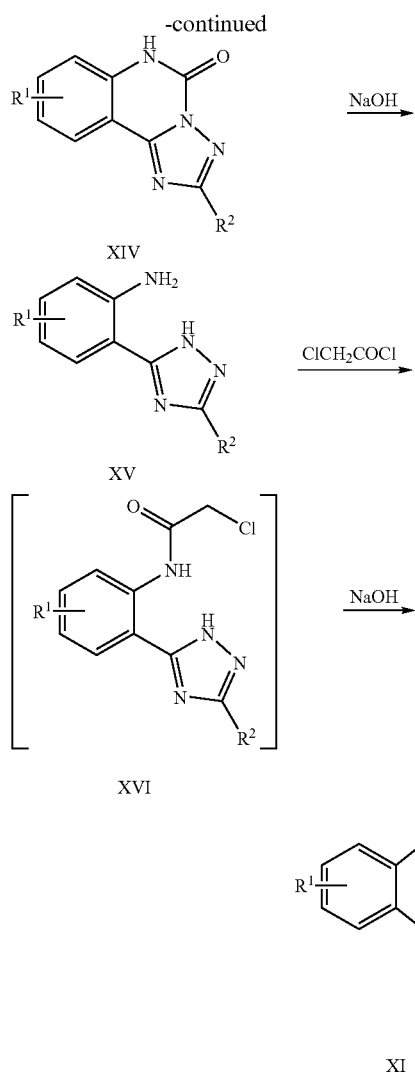

wherein $R^1$ and $R^2$ are as described above.

In accordance with scheme 2, a corresponding intermediate compound of formula XI can be prepared alternatively in the following way:

A corresponding compound of formula XII, an $R^1$-substituted 2-aminobenzonitrile, is heated with ethyl chloroformate to obtain a carbamic acid ester of formula XIII, which is treated with a compound of formula VI, an acylhydrazide, in 1-methyl-2-pyrrolidone at 160° C. under removal of ethanol. Conventional workup provides a urea of formula XIV, which is heated with aqueous sodium hydroxide in ethylenglycol to obtain a compound of formula XV. Treatment of a compound of formula XV with chloroacetyl chloride in acetic acid provides an amide of formula XVI, which is treated with aqueous sodium hydroxide in dioxane at ambient temperature to obtain the intermediate of formula XI. Alternatively, a compound of formula XV can be directly transformed to a compound of formula XI by dissolving a compound of formula XV in dioxane and pyridine and adding dropwise chloroacetyl chloride at a temperature between 10° C. to 15° C. After stirring for a short period of time, aqueous sodium hydroxide is added, and the reaction mixture stirred for several hours at ambient temperature to obtain the compound of formula XI.

Scheme 3

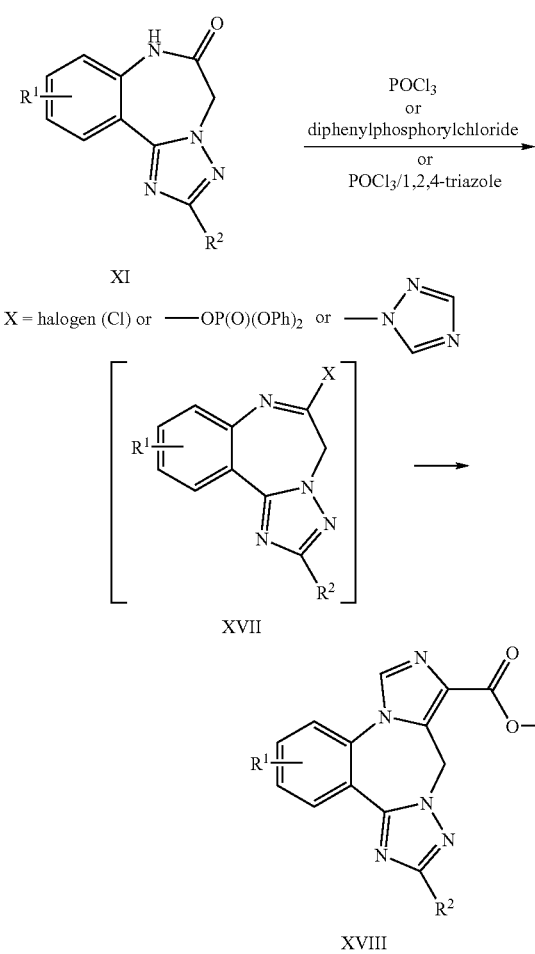

and R[1] and R[2] are as described above.

In accordance with scheme 3, a compound of formula XI is treated with an activation agent in the presence of base at elevated temperature, for example phosphorous oxide chloride in toluene or chloroform in the presence of N,N-dimethyl-p-toluidine, to obtain a compound of formula XVII, which is isolated in conventional manner or directly used in the next reaction step. Finally, a compound of formula XVIII is obtained by the reaction of XVII with a mixture of a cooled solution of lithium diisopropylamide or lithium hexamethyldisilazide in THF and (E)-(dimethylamino-methylenamino)- acetic acid ethyl ester or with a mixture of a cooled solution of ethyl isocyanoacetate in THF and potassium tert-butoxide or sodium hydride.

Scheme 4

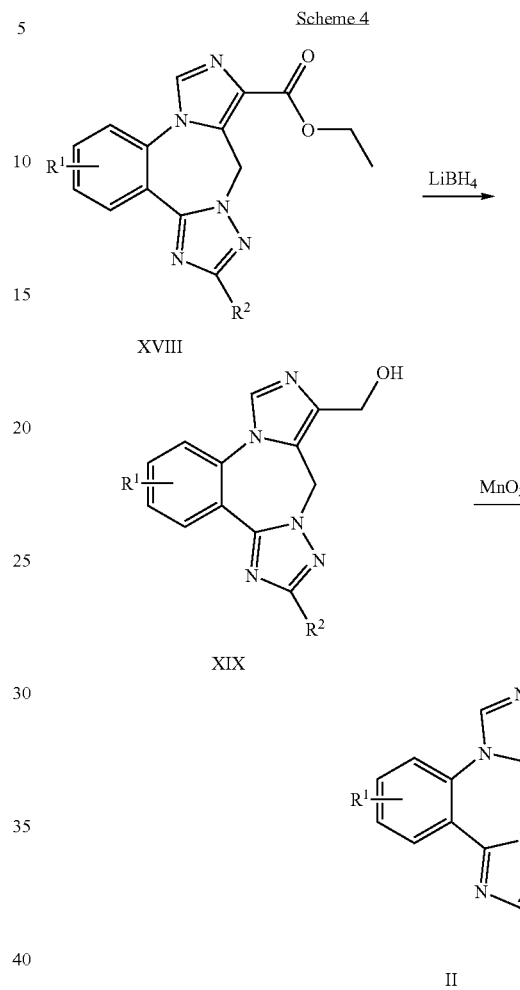

wherein R[1] and R[2] are as described above.

According to scheme 4, a compound of formula XVIII is heated with a reducing agent, for example lithiumborohydride or the like, in a suitable solvent, for example tetrahydrofuran or the like, to obtain an alcohol of formula XIX which is oxidized by treatment with manganese (IV) oxide in dichloromethane at ambient temperature to obtain an aldehyde of general formula II.

Scheme 5

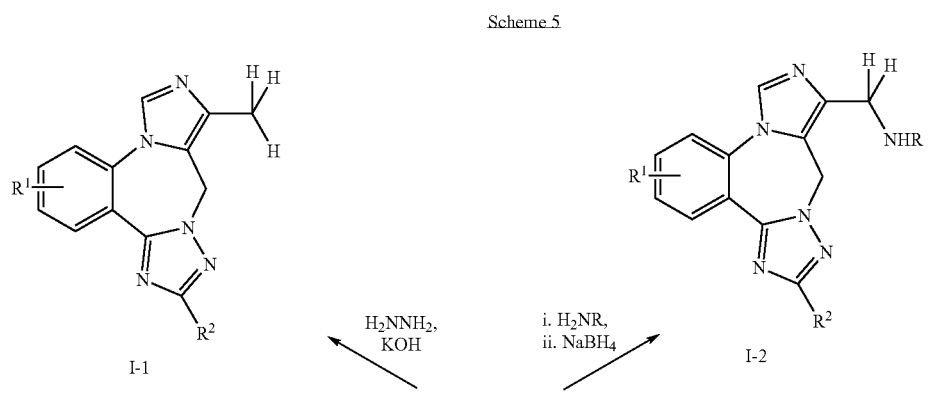

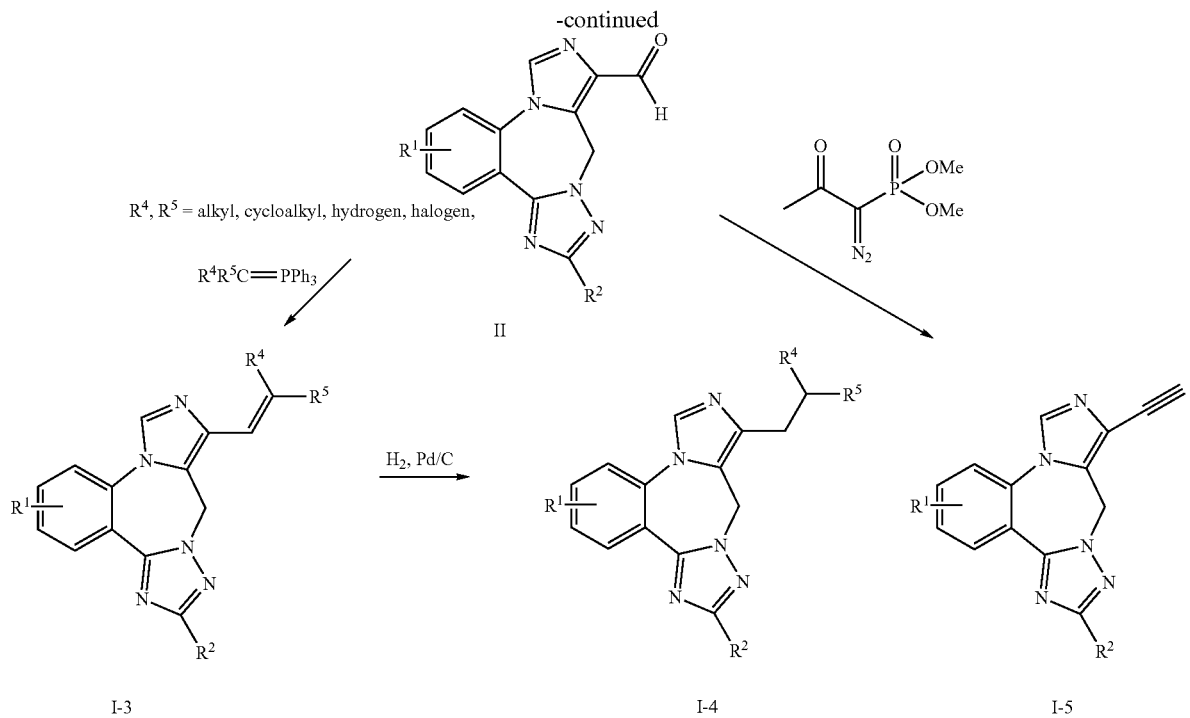

wherein $R^1$ and $R^2$ are as described above and R is cycloalkyl.

According to scheme 5, a compound of formula II could be transformed to a methyl-substituted compound of formula I-1 by Wolf-Kishner-reduction using hydrazine and potassium hydroxide in diethyleneglycol at elevated temperature. Reaction of II with a Wittig-type reagent, for example prepared in situ from methyltriphenylphosphonium bromide and sodium amide in tetrahydrofuran, at ambient temperature leads to an olefinic compound of general formula I-3 which could furthermore reduced using hydrogen and a palladium(0) catalyst, for example palladium(0) on charcoal, in a suitable solvent, for example ethanol, at ambient temperature to obtain a compound of general formula I-4. In addition, reaction of an aldehyde of formula II with dimethyl-1-diazo-2-oxopropylphosphonate and potassium carbonate as a base in methanol at ambient temperature provides a terminal alkyne compound of formula I-5. Methyleneamino-substituted compounds of formula I-2 can be obtained by reductive amination of aldehyde II via treatment of II with an suitable amine, for example cyclopropylamine, in dichloromethane at ambient temperature followed by an reducing agent, for example sodium borohydride, at elevated temperature.

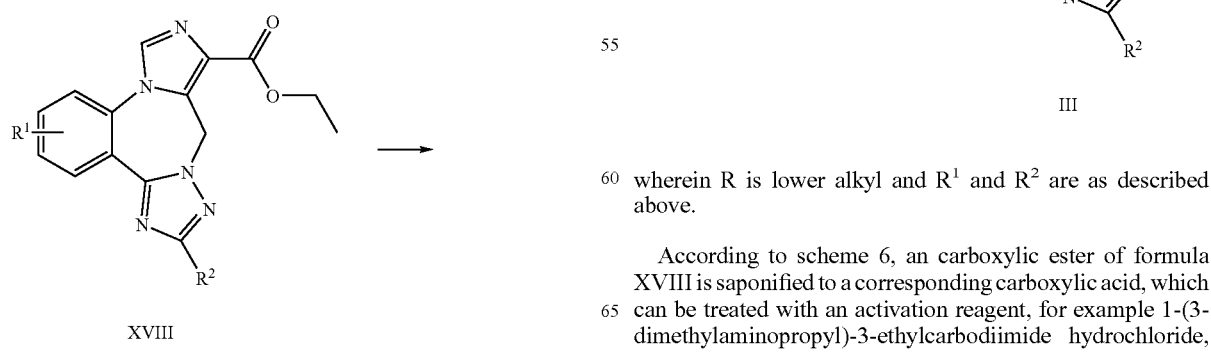

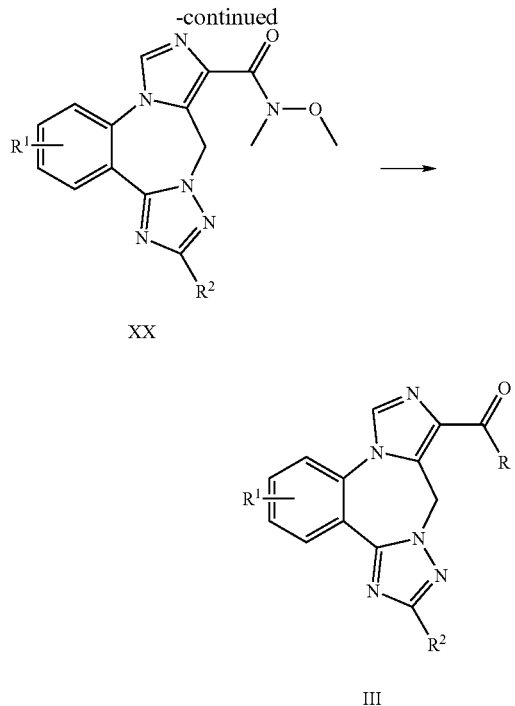

wherein R is lower alkyl and $R^1$ and $R^2$ are as described above.

According to scheme 6, an carboxylic ester of formula XVIII is saponified to a corresponding carboxylic acid, which can be treated with an activation reagent, for example 1-(3-dimethylaminopropyl)-3-ethylcarbodiimide hydrochloride, in the presence of N,O-dimethylhydroxylamine hydrochloride and a base, for example N-methylmorpholine, in a solvent mixture of dichloromethane and DMF at ambient temperature to afford a compound of formula XX. This amide of formula XX can be transformed to a corresponding ketone of general formula III by reaction with an appropriate Grignard reagent, for example methylmagnesium chloride, in a suitable solvent, for example THF or the like, at ambient or elevated temperature.

Scheme 7

III

I-6

I-7 wherein R is lower alkyl and $R^1$ and $R^2$ are as described above.

According to scheme 7, a compound of formula III can be transformed to an alkyl-substituted compound of formula I-6 by Wolf-Kishner-reduction using hydrazine and potassium hydroxide in diethyleneglycol at elevated temperature. Reduction of a ketone of formula III by treatment with a suitable reagent, for example sodium borohydride or the like, in a suitable solvent, for example methanol, at ambient temperature affords a secondary alcohol of general formula I-7.

Scheme 8

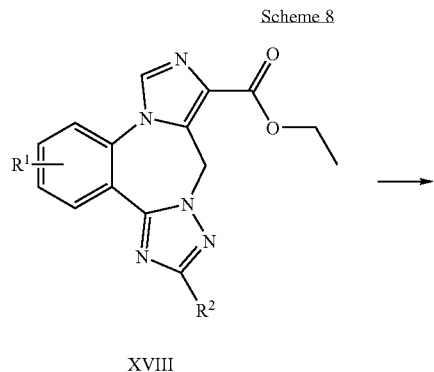

XVIII

XXI

IV wherein $R^1$ and $R^2$ are as described above.

According to scheme 8, a compound of formula XVIII is hydrolysed to the corresponding carboxylic acid, for example by treatment with sodium hydroxide in ethanol at elevated temperature, which is decarboxylated to a compound of formula XXI by stirring in an appropriate solvent, for example diethylene glycol dibutyl ether, at elevated temperature, for example 200° C. or the like, for some time. Finally, an iodo-substituted compound of formula IV can be obtained by reaction with an appropriate iodination reagent, for example N-iodosuccinimide, iodine or the like, in an appropriate solvent, for example N,N-dimethylformamide or dichloromethane or the like, at ambient or elevated temperature.

Scheme 9

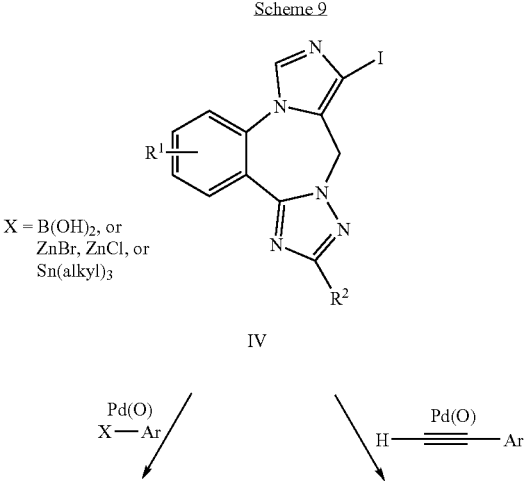

IV

X = B(OH)₂, or
ZnBr, ZnCl, or
Sn(alkyl)₃

Pd(O)
X—Ar

Pd(O)
H———Ar

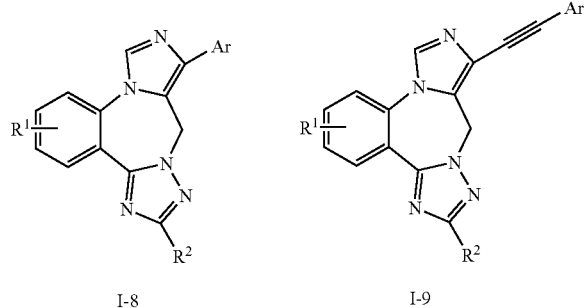

I-8  I-9 wherein $R^1$ and $R^2$ are as described above and Ar is unsubstituted or substituted phenyl or unsusbstituted or substituted pyridyl.

According to scheme 9, a compound of formula IV is transformed to an aryl- or heteroaryl-substituted compound of formula I-8 by treatment with an aryl/heteroaryl-boronic acid or aryl/heteroaryl-zinc halogenide, for example 6-methyl-2-pyridylzinc bromide, or an aryl/heteroaryl-tin reagent under palladium(0) catalysis in a suitable solvent, for example N,N-dimethylformamide, at elevated temperature. Alternatively, an aryl/heteroaryl-alkynyl-substituted compound of formula I-9 can be obtained by treatment of IV with an appropriate aryl/heteroaryl-alkyne, for example phenylacetylene, under palladium(0) and copper(I) catalysis in a suitable solvent, for example piperidine, at elevated temperature.

under palladium(0) and copper(I) catalysis in a suitable solvent, for THF, at elevated temperature. Alternatively, a compound of formula I-12 can be obtained from the corresponding fluoro-substituted compound of formula I-10 by treatment with an appropriate alkoxy-nucleophil, for example sodium methoxide, in a suitable solvent, for example DMSO, at elevated temperature.

Scheme 11

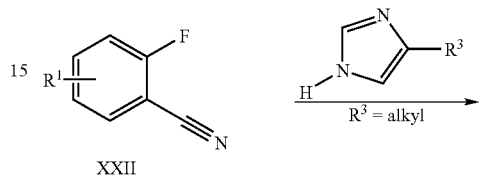

XXII

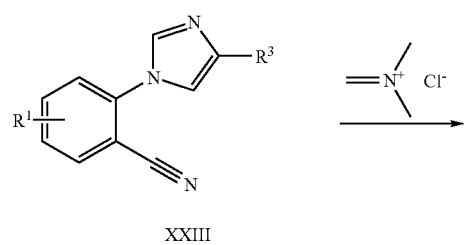

XXIII

Scheme 10

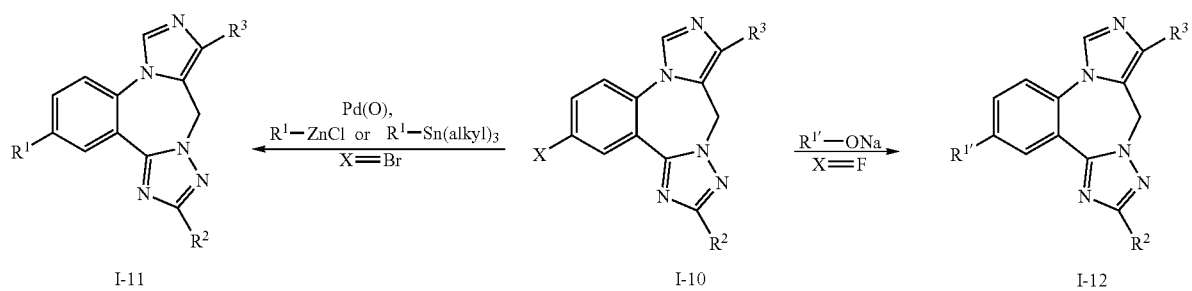

I-11  I-10  I-12

$R^1$ = alkyl,
cycloalkyl,
alkynyl wherein X is bromo or fluoro, $R^1$ is lower alkyl, cycloalkyl or —C≡C—R', $R^{1'}$ is lower alkoxy or —O(CH$_2$)$_m$O(CH$_2$)$_m$OH and the other substituents are as defined above.

According to scheme 10, a compound of formula I-11 can be obtained from the corresponding bromo-substituted compound of formula I-10 by treatment with an alkyl/cycloalkyl-zinc halogenide, for example cyclopropylzinc chloride, or a di-alkyl/cycloalkyl zinc reagent, for example diethylzinc, under palladium(0) catalysis in a suitable solvent, for example THF, at elevated temperature or by treatment with an appropriate alkyne, for example trimethylsilylacetylene, -continued

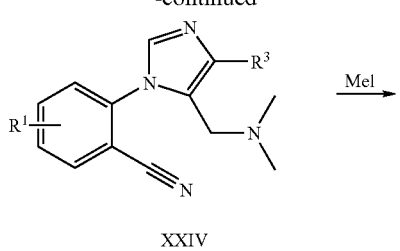

XXIV

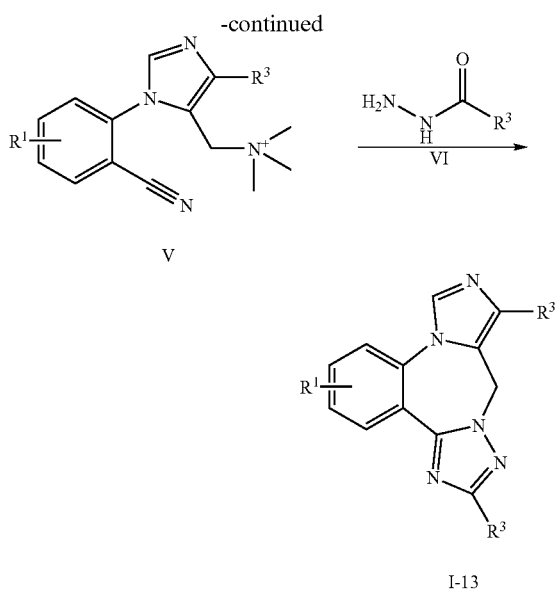

wherein $R^1$, $R^2$ are as described above and $R^3$ is lower alkyl.

In accordance with scheme 11, a compound of formula I ($R^3$=alkyl) can also be prepared in the following way:

Treatment of an appropriately substituted 2-fluorobenzonitrile of formula XXII with 4-alkylimidazole leads to the corresponding intermediate XXIII. Preferably, the reaction is run in an inert solvent, such as DMSO, at ambient temperature in the presence of a base, such as alkali carbonate. A compound of formula XXIII can then be reacted with Eschenmoser's salt in an inert solvent, such as DMF, to furnish a dimethylaminomethyl substituted imidazole of formula XXIV. Reacting a solution of a compound of formula XXIV in an appropriate solvent like methylene chloride with a methylating agent, such as methyl iodide, leads to a quarternary ammonium salt of formula V, which precipitates from the reaction mixture. Finally, treating a compound of formula V with an optionally substituted hydrazide of formula VI in an inert solvent, such as DMF, at elevated temperature leads to a compound of formula I-13, which can be isolated by crystallization from a suitable solvent, for example methanol.

As mentioned earlier, the compounds of formula I and their pharmaceutically usable salts possess valuable pharmacological properties. The compounds of the present invention are ligands for GABA A receptors containing the α5 subunit and are therefore useful in therapies where cognition enhancement is required.

The compounds were investigated in accordance with the test given hereinafter.

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition a1b3g2, a2b3g2, a3b3g2 and a5b3g2.

Cell pellets were suspended in Krebs-tris buffer (4.8 mM KCl, 1.2 mM CaCl2, 1.2 mM MgCl2, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell memebranes, [3H]flumazenil at a concentration of 1 nM for a1, a2, a3 subunits and 0.5 nM for a5 subunits and the test compound in the range of 10-10-3×10-6 M. Nonspecific binding was defined by 10-5 M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and all were found to possess a Ki value for displacement of [3H]flumazenil from a5 subunits of the rat GABA A receptor of 100 nM or less. In a preferred embodiment the compounds of the are binding selective for the a5 subunit relative to the a1, a2 and a3 subunit.

The major important difference is change from SF9 to HEK293 cells (which are human transiently transfected).

In the table below it is shown the activity data of some representative compounds:

| Example No. | Ki[nM] hα1 | Ki[nM] hα2 | Ki[nM] hα3 | Ki[nM] hα5 |
|---|---|---|---|---|
| 1 | 41.6 | 15.5 | 10.1 | 2.6 |
| 2 | 18.2 | 9.1 | 10.8 | 3.0 |
| 3 | 18.5 | 218.9 | 265.2 | 3.0 |
| 9 | 7.9 | 1.9 | 1.3 | 0.5 |
| 10 | 15.4 | 9.6 | 7.0 | 2.1 |
| 11 | 26.7 | 84.6 | 39.1 | 3.8 |
| 12 | 4.2 | 7.9 | 5.6 | 1.6 |
| 14 | 4.9 | 10.2 | 6.1 | 1.7 |
| 18 | 12.8 | 5.7 | 3.7 | 0.8 |
| 19 | 7.8 | 5.9 | 2.3 | 11 |
| 20 | 35.8 | 33.6 | 20.8 | 2.2 |
| 21 | 5.2 | 6.9 | 4.8 | 0.4 |
| 23 | 26.9 | 41.0 | 32.5 | 3.7 |
| 26 | 4.6 | 6.4 | 3.5 | 0.5 |
| 27 | 20.3 | 19.0 | 11.9 | 0.9 |
| 28 | 91.0 | | | 3.6 |
| 29 | 8.7 | | | 2.7 |
| 30 | 13.3 | | | 1.2 |
| 31 | 5.5 | 4.5 | 3.6 | 1.6 |
| 33 | 3.4 | | | 1.2 |
| 34 | 14.1 | | | 1.1 |
| 36 | 4.0 | | | 1.5 |
| 40 | 8.5 | 3.7 | 2.3 | 0.5 |
| 41 | 13.5 | 14.4 | 7.0 | 1.0 |
| 42 | 10.6 | | | 1.4 |
| 53 | 184 | 261 | 126 | 4.3 |
| 57 | 4.7 | 12.8 | 6.3 | 1.0 |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of the invention, but as a rule are not necessary. Suitable carriers for suppositories are, for example, natural or hardened oils, waxes, fats, semi-liquid liquid or liquid polyols and the like.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories, or parenterally, for example, in the form of injection solutions.

Compounds of the invention have a high affinity and selectivity for GABA A α5 receptor binding sites. The invention provides a method of enhancing cognition which comprises administering to an individual a therapeutically effective amount of a compound of formula I or a pharmaceutically acceptable salt thereof. The invention also provides a method of treating cognitive disorders which comprises administering to an individual a therapeutically effective amount of a compound of formula I or a pharmaceutically acceptable salt thereof. The invention also provides a method of treating Alzheimer's disease which comprises administering to an individual a therapeutically effective amount of a compound of formula I or a pharmaceutically acceptable salt thereof.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples are provided for illustration of the invention. They should not be considered as limiting the scope of the invention, but merely as being representative thereof.

EXAMPLE 1

10-Methyl-9H-imidazo[1,5-a][1,2,4]triazolo[1,5-d][1,4]benzodiazepine

A mixture of 3-bromo-10-methyl-9H-imidazo[1,5-a][1,2,4]triazolo[1,5-d][1,4]benzodiazepine (190 mg, 0.60 mmol) and palladium(0) (10% on charcoal, 64 mg, 0.06 mmol) in THF (5 mL) and methanol (5 mL) was stirred under a hydrogen atmosphere for 18 h at ambient temperature. The reaction mixture was filtered and concentrated. The residue was purified by chromatography (SiO$_2$, heptane:ethyl acetate:dichloromethane:methanol=75:15:10:0 to 0:70:10:20) affording the title compound (104 mg, 73%) as a white solid. MS: m/e=238.1 [M+H]$^+$.

EXAMPLE 2

3-Fluoro-10-methyl-9H-imidazo[1,5-a][1,2,4]triazolo[1,5-d][1,4]benzodiazepine a) 3-Fluoro-10-hydroxymethyl-9H-imidazo[1,5-a][1,2,4]triazolo[1,5-d][1,4]benzodiazepine To a suspension of ethyl 3-fluoro-9H-imidazo[1,5-a][1,2,4]triazolo[1,5-d][1,4]benzodiazepine-10-carboxylate (EP 519 307) (9.24 g, 29.5 mmol) in THF (300 mL) was added lithium borohydride (811 mg, 35.4 mmol), and the reaction mixture was heated to reflux for 8 h. After cooling to ambient temperature, it was acidified to pH=2 by adding aq HCl 1N. The solvent was evaporated, and the residue was taken in aq. NH$_4$OH (conc., 100 mL). The resulting solid were filtered off, washed with water (3×10 mL) and dried (60° C., vacuo) affording the title compound (6.53 g, 83%) as a white solid. MS: m/e=272.2 [M+H]$^+$.

b) 3-Fluoro-9H-imidazo[1,5-a][1,2,4]triazolo[1,5-d][1,4]benzodiazepine-10-carbaldehyde To a suspension of 3-fluoro-10-hydroxymethyl-9H-imidazo[1,5-a][1,2,4]triazolo[1,5-d][1,4]benzodiazepine (6.00 g, 22.1 mmol) in dichloromethane (200 mL) at 0° C. was added sodium bicarbonate (5.58 g, 66.4 mmol) and Dess-Martin periodinane (14.5 g, 33.2 mmol). After stirring at this temperature for 35 min it was allowed to warm to ambient temperature and stirred for another 1.5 h. Heptane (300 mL) and dichloromethane (100 mL) were added, and the orange suspension was stirred for additional 2 h. After filtration through Hyflo® it was carefully washed with dichloromethane and evaporated. Purification of the residue by chromatography (SiO$_2$, ethyl acetate:methanol=19:1) afforded the title compound (5.12 g, 86%) as an off-white solid. MS: m/e=270.3 [M+H]$^+$.

c) 3-Fluoro-10-methyl-9H-imidazo[1,5-a][1,2,4]triazolo[1,5-d][1,4]benzodiazepine To a suspension of 3-fluoro-9H-imidazo[1,5-a][1,2,4]triazolo[1,5-d][1,4]benzodiazepine-10-carbaldehyde (332 mg, 1.25 mmol) in diethylene glycol (3.6 mL) was added potassium hydroxide (140 mg, 2.5 mmol) and hydrazine monohydrate (486 μL, 10.0 mmol). The white suspension was stirred for 17 h at 150° C. before it was cooled to ambient temperature, diluted with water (50 mL) and extracted with ethyl acetate (150 mL). The organic layers were washed with brine (150 mL) and dried over sodium sulfate. Purification of the residue by chromatography (SiO$_2$, heptane:ethyl acetate: dichloromethane:methanol=75:15:10:0 to 0:80:10:10) afforded the title compound (68 mg, 21%) as a white solid. MS: m/e=256.3 [M+H]$^+$.

EXAMPLE 3

3-Chloro-10-methyl-9H-imidazo[1,5-a][1,2,4]triazolo[1,5-d][1,4]benzodiazepine

As described for example 2c, 3-chloro-9H-imidazo[1,5-a][1,2,4]triazolo[1,5-d][1,4]benzodiazepine-10-carbaldehyde (200 mg, 0.70 mmol), instead of 3-fluoro-9H-imidazo[1,5-a][1,2,4]triazolo[1,5-d][1,4]benzodiazepine-10-carbaldehyde, was converted to the title compound (130 mg, 68%) which was obtained as a white solid. MS: m/e=272.0 [M+H]$^+$.

EXAMPLE 4

3-Bromo-10-methyl-9H-imidazo[1,5-a][1,2,4]triazolo[1,5-d][1,4]benzodiazepine

As described for example 2c, 3-bromo-9H-imidazo[1,5-a][1,2,4]triazolo[1,5-d][1,4]benzodiazepine-10-carbaldehyde (598 mg, 1.25 mmol), instead of 3-fluoro-9H-imidazo[1,5-a][1,2,4]triazolo[1,5-d][1,4]benzodiazepine-10-carbaldehyde, was converted to the title compound (256 mg, 65%) which was obtained as a white solid. MS: m/e=316.1/318.0 [M+H]$^+$.

EXAMPLE 5

3-Bromo-6,10-dimethyl-9H-imidazo[1,5-a][1,2,4]triazolo[1,5-d][1,4]benzodiazepine a) 5-Bromo-2-(4-methyl-imidazol-1-yl)-benzonitrile A mixture of 5-bromo-2-fluoro-benzonitrile (25.0 g, 125 mmol), 4-methylimidazole (12.5 g, 152 mmol), potassium carbonate (34.55 g, 250 mmol) in DMSO (500 mL) was stirred at 90° C. for 16 h. Water (1.5 L) was added and the resulting suspension was stirred with ice-bath cooling for 1 h. The precipitate was filtered, washed with water (0.5 L) and dried at 50° C. over KOH. The resulting raw material (25.6 g) was dissolved in boiling Ethyl acetate (300 ml). After addition of diisopropylether (300 ml) the solution was allowed to cool to room temperature. Filtration and drying afforded the title compound (19.35 g, 59%) as a white solid. Mp 166° C.

b) 5-Bromo-2-(5-dimethylaminomethyl-4-methyl-imidazol-1-yl)-benzonitrile

A solution of 5-bromo-2-(4-methyl-imidazol-1-yl)-benzonitrile (11.0 g, 42.0 mmol) and N,N-dimethylmethyleneiminium chloride (5.0 g, 53.4 mmol) in DMF (75 mL) was stirred at 90° C. for 16 h. The solvent was evaporated, and the oily residue was partitioned between saturated aqueous sodium bicarbonate solution and Ethyl acetate. The organic phase was dried over sodium sulfate, concentrated and purified by chromatography (SiO$_2$, gradient CH$_2$Cl$_2$ to 35% (CH$_2$Cl$_2$/MeOH=9/1) to afford the tide compound as an oil that solidifies on standing (10.62 g, 79%). MS: m/e=319.2/321.3 [M+H]$^+$.

c) [3-(4-Bromo-2-cyano-phenyl)-5-methyl-3H-imidazol-4-ylmethyl]-trimethyl-ammonium; iodide A solution of 5-bromo-2-(5-dimethylaminomethyl-4-methyl-imidazol-1-yl)-benzonitrile (5.57 g, 17.4 mmol) in CH$_2$Cl$_2$ (130 mL) was treated with methyl iodide (1.3 mL, 20.9 mmol) and kept at 4° C. for 72 h. The white crystalline material formed was filtered and dried (6.4 g, 80%). MS: m/e=333.2/335.2 [M]$^+$.

d) 3-Bromo-6,10-dimethyl-9H-imidazo[1,5-a][1,2,4]triazolo[1,5-d][1,4]benzodiazepine A mixture of [3-(4-bromo-2-cyano-phenyl)-5-methyl-3H-imidazol-4-ylmethyl]-trimethyl-ammonium; iodide (462 mg, 1 mmol) and acetic hydrazide (74 mg, 1.2 mmol) in DMF (5 ml) was stirred at 120° C. for 16 h, then the mixture was heated to 150° C. for another 12 h. After cooling to rt water (20 mL) was added, the precipitate filtered and dried. Recrystallisation from Ethyl acetate affords the title compound as a yellow crystalline material (47 mg, 14%). MS: m/e=332.0 [M+H]$^+$.

EXAMPLE 6

10-Ethyl-9H-imidazo[1,5-a][1,2,4]triazolo[1,5-d][1,4]benzodiazepine

A solution of 10-vinyl-9H-imidazo[1,5-a][1,2,4]triazolo[1,5-d][1,4]benzodiazepine (Example 18) (85 mg, 0.34 mmol) in methanol (10 ml) and THF (3.5 ml) was flushed with argon. Pd/C (10%, 36 mg, 0.03 mmol) was added, and the mixture was stirred for 23 h at ambient temperature under a hydrogen atmosphere. It was filtered over Hyflo®, washed with methanol and was evaporated. Purification of the residue by chromatography (SiO$_2$, heptane:ethyl acetate:dichloromethane:methanol=75:15:10:0 to 0:70:10:20) afforded the title compound (67 mg, 79%) as a white solid. MS: m/e=252.2 [M+H]$^+$.

EXAMPLE 7

3-Cyclopropyl-10-methyl-9H-imidazo[1,5-a][1,2,4]triazolo[1,5-d][1,4]benzodiazepine To a suspension of 3-bromo-10-methyl-9H-imidazo[1,5-a][1,2,4]triazolo[1,5-d][1,4]benzodiazepine (190 mg, 0.60 mmol) in THF (5 mL) was added under an argon atmosphere tetrakis(triphenylphosphine)palladium(0) (35 mg, 0.03 mmol) and cyclopropylzinc chloride (0.5 M in THF, 1.5 mL, 0.75 mmol). After stirring for 18 h at ambient temperature it was added further tetrakis(triphenylphosphine)palladium(0) (70 mg, 0.06 mmol) and cyclopropylzinc chloride (0.5 M in THF, 3.0 mL, 1.5 mmol), and the mixture was stirred for 23 h at 60° C. The reaction mixture was diluted with ethyl acetate (30 mL) and was washed with aqueous sodium carbonate (sat., 25 mL) and water (25 mL). The aqueous layer was extracted with ethyl acetate (30 mL), and the combined organic layers were dried over sodium sulfate. Purification of the residue by chromatography (SiO$_2$, heptane:ethyl acetate:dichloromethane:methanol=75:15:10:0 to 0:80:10:10) afforded the title compound (25 mg, 15%) as a white foam. MS: m/e=238.1 [M+H]$^+$.

EXAMPLE 8

3-Ethynyl-10-methyl-9H-imidazo[1,5-a][1,2,4]triazolo[1,5-d][1,4]benzodiazepine a) 10-Methyl-3-trimethylsilyanylethynyl-9H-imidazo[1,5-a][1,2,4]triazolo[1,5-d][1,4]benzodiazepine A suspension of 3-bromo-10-methyl-9H-imidazo[1,5-a][1,2,4]triazolo[1,5-d][1,4]benzodiazepine (316 mg, 1.00 mmol), trimethylsilylacetylene (221 μL, 1.55 mmol), bis(triphenylphosphine)-palladium(II) chloride (35 mg, 0.05 mmol), triphenylphosphine (8 mg, 0.03 mmol) and triethylamine (0.50 mL, 3.6 mmol) in THF (5 mL) was stirred for 15 min at ambient temperature. Copper(I) bromide (1.4 mg, 0.01 mmol) was added, and the reaction mixture was stirred for 23 h at 70° C. under an argon atmosphere. The mixture was diluted with ethyl acetate (20 mL) and washed with aqueous citric acid (10%, 40 mL). The aqueous phase was extracted with ethyl acetate (40 mL) and the combined organic layers were dried over sodium sulfate. Purification by chromatography (SiO$_2$, heptane:ethyl acetate:dichloromethane:methanol=75:15:10:0 to 0:80:10:10) afforded the title compound (332 mg, 99%) as a yellow foam. MS: m/e=334.2 [M+H]$^+$.

b) 3-Ethynyl-10-methyl-9H-imidazo[1,5-a][1,2,4]triazolo[1,5-d][1,4]benzodiazepine To a solution of 10-methyl-3-trimethylsilanylethynyl-9H-imidazo[1,5-a][1,2,4]triazolo[1,5-d]-[1,4]benzodiazepine (332 mg, 1.00 mmol) in a mixture of THF (3.6 mL) and MeOH (0.36 mL) was added under an argon atmosphere at −70° C. tetrabutylammonium fluoride trihydrate (331 mg, 1.05 mmol). After stirring for 30 min at this temperature, the dry ice bath was replaced with an ice bath and the reaction mixture was stirred for 2 h at 0° C. It was diluted with ethyl acetate (20 mL), washed with aqueous Na$_2$CO$_3$ and extracted with ethyl acetate (20 mL). Drying over sodium sulfate and purification by chromatography (SiO$_2$, heptane:ethyl acetate:dichloromethane:methanol=75:15:10:0 to 0:80:10:10) afforded the title compound (184 mg, 70%) as an off-white solid. MS: m/e=262.1 [M+H]$^+$.

EXAMPLE 9

10-Ethyl-3-fluoro-9H-imidazo[1,5-a][1,2,4]triazolo[1,5-d][1,4]benzodiazepine

To a suspension of 3-fluoro-10-vinyl-9H-imidazo[1,5-a][1,2,4]triazolo[1,5-d][1,4]benzodiazepine (200 mg, 0.75 mmol) in ethanol (2 mL) was added palladium(0) (10% on charcoal, 20 mg, 0.19 mmol) and stirred for 18 h at ambient temperature under a hydrogene atmosphere. The reaction mixture was filtered over Hyflo® and washed with ethanol. Purification by chromatography (SiO$_2$, ethyl acetate:methanol=100:0 to 90:10) afforded the title compound (181 mg, 90%) as a white solid. MS: m/e=270.3 [M+H]$^+$.

EXAMPLE 10

3-Chloro-10-ethyl-9H-imidazo[1,5-a][1,2,4]triazolo[1,5-d][1,4]benzodiazepine

To a solution of 3-chloro-10-vinyl-9H-imidazo[1,5-a][1,2,4]triazolo[1,5-d][1,4]benzodiazepine (270 mg, 0.95 mmol) in THF (5 mL) was added palladium(0) (10% on charcoal, 20 mg, 0.19 mmol) and was stirred for 3 h at ambient temperature under a hydrogene atmosphere. The reaction mixture was filtered over Hyflo® and washed with THF. Purification by chromatography (SiO$_2$, heptane:ethyl acetate:dichloromethane:methanol=50:30:20:0 to 0:75:20:5) afforded the title compound (58 mg, 20%) as a white solid. MS: m/e=286.1 [M+H]$^+$.

EXAMPLE 11

10-Ethyl-3-methoxy-9H-imidazo[1,5-a][1,2,4]triazolo[1,5-d][1,4]benzodiazepine

To a solution of 10-ethyl-3-fluoro-9H-imidazo[1,5-a][1,2,4]triazolo[1,5-d][1,4]benzodiazepine (120 mg, 0.45 mmol) in DMSO (1.2 mL) was added sodium methoxide (120 mg, 2.22 mmol), and the solution was stirred for 4 h at 130° C. The reaction mixture was diluted with ethyl acetate (20 mL), washed with aqueous sodium carbonate (sat.) and was extracted with ethyl acetate (20 mL). Drying over sodium sulfate and purification by chromatography (SiO$_2$, heptane:ethyl acetate:dichloromethane=80:20:0 to 0:90:10) afforded the title compound (99 mg, 79%) as a white solid. MS: m/e=282.1 [M+H]$^+$.

EXAMPLE 12

3-Chloro-10-propyl-9H-imidazo[1,5-a][1,2,4]triazolo[1,5-d][1,4]benzodiazepine

As described for example 2c, 1-[3-chloro-9H-imidazo[1,5-a][1,2,4]triazolo[1,5-d][1,4]benzodiazepin-10-yl]-propan-1-one (98 mg, 0.32 mmol), instead of 3-fluoro-9H-imidazo[1,5-a][1,2,4]triazolo[1,5-d][1,4]benzodiazepine-10-carbaldehyde, was converted to the title compound (87 mg, 93%) which was obtained as a light brown solid. MS: m/e=300.1 [M+H]$^+$.

EXAMPLE 13

3-Chloro-10-cyclopropyl-9H-imidazo[1,5-a][1,2,4]triazolo[1,5-d][1,4]benzodiazepine a) 3-Chloro-9H-imidazo[1,5-a][1,2,4]triazolo[1,5-d][1,4]benzodiazepine A suspension of 3-chloro-9H-imidazo[1,5-a][1,2,4]triazolo[1,5-d][1,4]benzo-diazepine-10-carboxylic acid (EP 519 307) (17.5 g, 57.8 mmol) in diethylene glycol dibutyl ether (200 mL) was stirred for 62 h at 200° C. under a nitrogen-atmosphere. The resulting suspension was treated with 770 mL heptane and stirred for 1.5 h at 0° C. Filtration and washing with heptane (2×100 mL) afforded the title compound (14.1 g, 94%) as an off-white solid. MS: m/e=258.0 [M+H]$^+$.

b) 3-Chloro-10-iodo-9H-imidazo[1,5-a][1,2,4]triazolo[1,5-d][1,4]benzodiazepine

To a solution of 3-chloro-9H-imidazo[1,5-a][1,2,4]triazolo[1,5-d][1,4]benzodiazepine (7.40 g, 28.7 mmol) in dimethylformamide (240 mL) was added iodine (14.6 g, 57.5 mmol). The resulting mixture was stirred for 6 d at 55° C. before water (3 L) and aqueous Na$_2$S$_2$O$_3$ (10%, 500 mL) were added and the mixture extracted with dichloromethane. Drying over sodium sulfate and purification by chromatography (SiO$_2$, dichloromethane:ethanol=100:0 to 97:3) afforded the title compound (3.10 g, 35%) as a white crystalline solid. MS: m/e=383.9 [M]$^+$.

c) 3-Chloro-10-cyclopropyl-9H-imidazo[1,5-a][1,2,4]triazolo[1,5-d][1,4]benzodiazepine To a suspension of 3-chloro-10-iodo-9H-imidazo[1,5-a][1,2,4]triazolo[1,5-d][1,4]benzodiazepine (200 mg, 0.52 mmol) in THF (5 mL) was added under an argon atmosphere tetrakis(triphenylphosphine)palladium(0) (30 mg, 0.026 mmol) and cyclopropylzinc chloride (0.38 M in THF, 3.4 mL, 1.3 mmol), and the mixture was stirred for 3 h at ambient temperature. The reaction mixture was diluted with ethyl acetate (30 mL) and was washed with aqueous sodium carbonate (sat., 25 mL) and water (25 mL). The aqueous layer was extracted with ethyl acetate (30 mL), and the combined organic layers were dried over sodium sulfate. Purification of the residue by chromatography (SiO$_2$, heptane:ethyl acetate:dichloromethane=60:20:20 to 10:70:20) afforded the title compound (33 mg, 21%) as a white solid. MS: m/e=298.0 [M+H]$^+$.

EXAMPLE 14

3-Chloro-10-cyclopropylmethyl-9H-imidazo[1,5-a][1,2,4]triazolo[1,5-d][1,4]benzodiazepine As described for example 2c, cyclopropyl-[3-chloro-9H-imidazo[1,5-a][1,2,4]triazolo[1,5-d][1,4]benzodiazepin-10-yl]-methanone (400 mg, 1.23 mmol), instead of 3-fluoro-9H-imidazo[1,5-a][1,2,4]triazolo[1,5-d][1,4]benzodiazepine-10-carbaldehyde, was converted to the title compound (182 mg, 48%) which was obtained as a white foam. MS: m/e=312.0 [M+H]$^+$.

EXAMPLE 15

10-Cyclopropylmethyl-3-[2-(2-hydroxy-ethoxy)-ethoxy]-9H-imidazo[1,5-a][1,2,4]triazolo[1,5-d][1,4]benzodiazepine As described for example 2c, cyclopropyl-[3-fluoro-9H-imidazo[1,5-a][1,2,4]triazolo[1,5-d][1,4]benzodiazepin-10-yl]-methanone (400 mg, 1.29 mmol), instead of 3-fluoro-9H-imidazo[1,5-a][1,2,4]triazolo[1,5-d][1,4]benzodiazepine-10-carbaldehyde, was converted to the title compound (170 mg, 34%) which was obtained as a light yellow oil. MS: m/e=282.2 [M+H]$^+$.

EXAMPLE 16

1-[3-chloro-9H-imidazo[1,5-a][1,2,4]triazolo[1,5-d][1,4]benzodiazepin-10-yl]-propan-1-ol To a suspension o 1-[3-chloro-9H-imidazo[1,5-a][1,2,4]triazolo[1,5-d][1,4]benzodiazepin-10-yl]-propan-1-one (777 mg, 2.48 mmol) in methanol (5 mL) was added sodium borohydride (141 mg, 3.72 mmol), and the reaction mixture was stirred for 18 h at ambient temperature. It was diluted with dichloromethane and washed with aqueous sodium carbonate (1 N). The aqueous layers were extracted with dichloromethane, and the combined organic layers were dried over sodium sulfate. After addition of toluene the dichloromethane was distilled off, and the resulting white suspension was filtered. Washing of the residue with toluene afforded the title compound (656 mg, 83%) as a white solid. MS: m/e=316.0 [M+H]$^+$.

EXAMPLE 17

3-Chloro-10-cyclopropylaminomethyl-9H-imidazo[1,5-a][1,2,4]triazolo[1,5-d][1,4]benzodiazepine To a suspension of 3-chloro-9H-imidazo[1,5-a][1,2,4]triazolo[1,5-d][1,4]benzodiazepine-10-carbaldehyde (200 mg, 0.76 mmol) and magnesium sulfate (400 mg, 3.32 mmol) in dichloromethane (2 mL) was added cyclopropylamine (80 μL, 1.13 mmol), and the reaction mixture was stirred for 18 h at ambient temperature. Toluene (2 mL) was added and stirring was continued for 3 d at 100° C. After addition of sodium borohydride (57 mg, 1.51 mmol) and methanol (2 mL) the resulting mixture was stirred for 24 h at ambient temperature. It was diluted with aqueous sodium carbonate (1 N) and extracted with dichloromethane. Drying over sodium sulfate and purification by chromatography (SiO$_2$, dichloromethane:(dichloromethane:methanol:ammonia=70:27:3)=95:5 to 90:10) afforded the title compound (108 mg, 44%) as a white solid. MS: m/e=327.0 [M+H]$^+$.

EXAMPLE 18

10-Vinyl-9H-imidazo[1,5-a][1,2,4]triazolo[1,5-d][1,4]benzodiazepine

A mixture of methyltriphenylphosphonium bromide/sodium amide (793 mg, 2.00 mmol) in THF (4.3 mL) was stirred for 15 min at ambient temperature. 9H-imidazo[1,5-a][1,2,4]triazolo[1,5-d][1,4]benzodiazepine-10-carbaldehyde (251 mg, 1.00 mmol) was added, and sirring was continued for 5.5 h at this temperature. The resulting suspension was filtered, washed with THF and concentrated. Purification by chromatography (SiO$_2$, heptane:ethyl acetate:dichloromethane:methanol=75:15:10:0 to 0:80:10:10) afforded the title compound (28 mg, 11%) as a white solid. MS: m/e=250.2 [M+H]$^+$.

EXAMPLE 19

3-Fluoro-10-vinyl-9H-imidazo[1,5-a][1,2,4]triazolo[1,5-d][1,4]benzodiazepine

As described for example 18, 3-fluoro-9H-imidazo[1,5-a][1,2,4]triazolo[1,5-d][1,4]benzodiazepine-10-carbaldehyde (3.5 g, 13.0 mmol), instead of 9H-imidazo[1,5-a][1,2,4]triazolo[1,5-d][1,4]benzodiazepine-10-carbaldehyde, was converted to the title compound (2.45 g, 71%) which was obtained as a light yellow crystalline solid. MS: m/e=268.3 [M+H]$^+$.

EXAMPLE 20

3-Chloro-10-vinyl-9H-imidazo[1,5-a][1,2,4]triazolo[1,5-d][1,4]benzodiazepine

As described for example 18, 3-chloro-9H-imidazo[1,5-a][1,2,4]triazolo[1,5-d][1,4]benzodiazepine-10-carbaldehyde (200 mg, 0.70 mmol), instead of 9H-imidazo[1,5-a][1,2,4]triazolo[1,5-d][1,4]benzodiazepine-10-carbaldehyde, was converted to the title compound (98 mg, 49%) which was obtained as a white solid. MS: m/e=284.0 [M+H]$^+$.

EXAMPLE 21

3-Chloro-10-(E)-propenyl-9H-imidazo[1,5-a][1,2,4]triazolo[1,5-d][1,4]benzodiazepine A suspension of 3-chloro-9H-imidazo[1,5-a][1,2,4]triazolo[1,5-d][1,4]benzodiazepine-10-carbaldehyde (200 mg, 0.70 mmol), potassium carbonate (290 mg, 2.10 mmol) and ethyl triphenylphosphonium bromide (312 mg, 0.84 mmol) in dioxane (2 mL) was irradiated in the microwave for 20 min at 150° C. The reaction mixture was filtered, washed with dioxane (5 mL) and was concentrated. Purification by chromatography (SiO$_2$, ethyl acetate:dichloromethane=1:1) afforded the title compound (33 mg, 16%) as a white solid. MS: m/e=298.0 [M+H]$^+$.

EXAMPLE 22

3-Chloro-10-(Z)-propenyl-9H-imidazo[1,5-a][1,2,4]triazolo[1,5-d][1,4]benzodiazepine A suspension of 3-chloro-9H-imidazo[1,5-a][1,2,4]triazolo[1,5-d][1,4]benzodiazepine-10-carbaldehyde (200 mg, 0.70 mmol), potassium carbonate (290 mg, 2.10 mmol), and ethyl triphenylphosphonium bromide (312 mg, 0.84 mmol) in dioxane (2 mL) was irradiated in the microwave for 20 min at 150° C. The reaction mixture was filtered, washed with dioxane (5 mL) and was concentrated. Purification by chromatography (SiO$_2$, ethyl acetate:dichloromethane=1:1) afforded the title compound (42 mg, 20%) as a white solid. MS: m/e=298.0 [M+H]$^+$.

EXAMPLE 23

3-Chloro-10-((E)-2-cyclopropyl-vinyl)-9H-imidazo[1,5-a][1,2,4]triazolo[1,5-d][1,4]benzodiazepine A suspension of 3-chloro-9H-imidazo[1,5-a][1,2,4]triazolo[1,5-d][1,4]benzodiazepine-10-carbaldehyde (200 mg, 0.70 mmol), potassium carbonate (290 mg, 2.10 mmol) and cyclopropyl triphenylphosphonium bromide (333 mg, 0.84 mmol) in DMF (2 mL) was stirred for 18 h at ambient temperature and 24 h at 90° C. The reaction mixture was diluted with ethyl acetate (20 mL) and washed with aqueous sodiumcarbonate (sat.). Drying over sodium sulfate and purification by chromatography (SiO$_2$, heptane:ethyl acetate:dichloromethane=60:20:20 to 30:50:20) afforded the title compound (16 mg, 7%) as a white solid. MS: m/e=324.2 [M+H]$^+$.

EXAMPLE 24

3-Chloro-10-((Z)-2-cyclopropyl-vinyl)-9H-imidazo[1,5-a][1,2,4]triazolo[1,5-d][1,4]benzodiazepine A suspension of 3-chloro-9H-imidazo[1,5-a][1,2,4]triazolo[1,5-d][1,4]benzodiazepine-10-carbaldehyde (200 mg, 0.70 mmol), potassium carbonate (290 mg, 2.10 mmol) and cyclopropyl triphenylphosphonium bromide (333 mg, 0.84 mmol) in DMF (2 mL) was stirred for 18 h at ambient temperature and 24 h at 90° C. The reaction mixture was diluted with ethyl acetate (20 mL) and washed with aqueous sodium carbonate (sat.). Drying over sodium sulfate and purification by chromatography (SiO$_2$, heptane:ethyl acetate:dichloromethane=60:20:20 to 30:50:20) afforded the title compound (58 mg, 26%) as a white solid. MS: m/e=324.2 [M+H]$^+$.

EXAMPLE 25

10-Ethynyl-3-fluoro-9H-imidazo[1,5-a][1,2,4]triazolo[1,5-d][1,4]benzodiazepine

As described for example 27, 3-fluoro-9H-imidazo[1,5-a][1,2,4]triazolo[1,5-d][1,4]benzodiazepine-10-carbaldehyde (600 mg, 2.23 mmol), instead of 3-bromo-9H-imidazo[1,5-a][1,2,4]triazolo[1,5-d][1,4]benzodiazepine-10-carbaldehyde, was converted to the tide compound (470 mg, 80%) which was obtained as an off-white solid. MS: m/e=265.1 [M]$^+$.

EXAMPLE 26

3-Chloro-10-ethynyl-9H-imidazo[1,5-a][1,2,4]triazolo[1,5-d][1,4]benzodiazepine

To a suspension of 3-chloro-10-(3-hydroxy-3-methyl-but-1-ynyl)-9H-imidazo[1,5-a][1,2,4]triazolo[1,5-d][1,4]benzodiazepine (212 mg, 0.62 mmol) in toluene (2 mL) was added potassium hydroxide (14 mg, 0.25 mmol), and the reaction mixture was stirred for 2 h at 110° C. Purification of the reaction mixture by chromatography (SiO$_2$, heptane:ethyl acetate=80:20 to 0:100) afforded the title compound (120 mg, 68%) as a white solid. MS: m/e=282.1 [M+H]$^+$.

EXAMPLE 27

3-Bromo-10-ethynyl-9H-imidazo[1,5-a][1,2,4]triazolo[1,5-d][1,4]benzodiazepine

To a suspension of 3-bromo-9H-imidazo[1,5-a][1,2,4]triazolo[1,5-d][1,4]benzodiazepine-10-carbaldehyde (1.08 g, 3.27 mmol) in methanol (45 mL) was added dimethyl-1- diazo-2-oxopropylphosphonate (878 mg, 4.57 mmol) and potassium carbonate (903 mg, 6.53 mmol), and the reaction mixture was stirred for 19 h at ambient temperature and was then poured onto aqueous sodium hydrogen carbonate (0.5 M, 125 mL). It was extracted with ethyl acetate (600 mL), and the organic layers were dried over sodium sulfate. Trituration in ethyl acetate (10 mL) afforded the title compound (453 mg, 43%) as a white solid. MS: m/e=326.1/327.9 [M+H]$^+$.

EXAMPLE 28

3-Chloro-10-(3-hydroxy-3-methyl-but-1-ynyl)-9H-imidazo[1,5-a][1,2,4]triazolo[1,5-d][1,4]benzodiazepine To a mixture of 3-chloro-10-iodo-9H-imidazo[1,5-a][1,2,4]triazolo[1,5-d][1,4]benzodiazepine (3.00 g, 7.82 mmol), bis(triphenylphosphine)palladium(II) chloride (150 mg, 0.21 mmol) in diethylamine (90 mL) was added copper(I) iodide (100 mg, 0.53 mmol) and 2-methyl-3-butin-2-ol (3.00 mL, 30.7 mmol), and the resulting suspension was stirred for 1 h at 65° C. The reaction mixture was concentrated, and purification of the residue by chromatography (SiO$_2$, dichloromethane:methanol=99:1 to 97:3) afforded the title compound (2.40 g, 90%) as a white crystalline solid. MS: m/e=340.1 [M+H]$^+$.

EXAMPLE 29

3-Fluoro-10-phenylethynyl-9H-imidazo[1,5-a][1,2,4]triazolo[1,5-d][1,4]benzodiazepine To a mixture of 3-fluoro-10-iodo-9H-imidazo[1,5-a][1,2,4]triazolo[1,5-d][1,4]benzodiazepine (1.10 g, 2.99 mmol) in diethylamine (15 mL) and DMF (7 mL) were added bis(triphenylphosphine)palladium(II) chloride (25 mg, 0.04 mmol), copper(I) iodide (4 mg, 0.02 mmol) and phenylacetylene (0.37 mL, 3.3 mmol), and the resulting suspension was stirred for 1 h at 65° C. The reaction mixture was concentrated and dissolved in dichloromethane, washed with water and dried over sodium sulfate. Purification by chromatography (SiO$_2$, dichloromethane:ethanol=100:0 to 98.5:1.5) afforded the title compound (820 mg, 80%) as a colourless crystalline solid. MS: m/e=342.2 [M+H]$^+$.

EXAMPLE 30

3-Chloro-10-phenylethynyl-9H-imidazo[1,5-a][1,2,4]triazolo[1,5-d][1,4]benzodiazepine To a mixture of 3-chloro-10-iodo-9H-imidazo[1,5-a][1,2,4]triazolo[1,5-d][1,4]benzodiazepine (100 mg, 0.26 mmol), triphenylphosphine (21 mg, 0.01 mmol) and bis(triphenylphosphine)palladium(II) chloride (9.1 mg, 0.01 mmol) was added piperidine (1 mL), and the resulting suspension was stirred for 15 min under an argon atmosphere. Copper(I) iodide (0.5 mg, 0.003 mmol) and phenylacetylene (43 µL, 0.39 mmol) were added, and stirring was continued for 18 h at ambient temperature. The reaction mixture was heated to 50° C. for 30 min before diluting with water and extraction with ethyl acetate. The combined organic layers were washed with aqueous sodium chloride (sat.) and dried over sodium sulfate. Purification by chromatography (SiO$_2$, hexane:ethyl acetate=90:10 to 50:50) afforded the title compound (89 mg, 91%) as a light brown solid. MS: m/e=357.0 [M]$^+$.

EXAMPLE 31

3-Fluoro-10-(3-fluoro-phenylethynyl)-9H-imidazo[1,5-a][1,2,4]triazolo[1,5-d][1,4]benzodiazepine As described for example 30, 10-ethynyl-3-fluoro-9H-imidazo[1,5-a][1,2,4]triazolo[1,5-d][1,4]benzodiazepine (250 mg, 0.94 mmol), instead of phenylacetylene using 1-fluoro-3-iodo-benzene instead of 3-chloro-10-iodo-9H-imidazo[1,5-a][1,2,4]triazolo[1,5-d][1,4]benzodiazepine, was converted to the title compound (SiO$_2$, heptane:ethyl acetate=90:10 to 40:60, 255 mg, 75%) which was obtained as a white solid. MS: m/e=360.2 [M+H]$^+$.

EXAMPLE 32

3-Fluoro-10-(3-chloro-phenylethynyl)-9H-imidazo[1,5-a][1,2,4]triazolo[1,5-d][1,4]benzodiazepine As described for example 30, 10-ethynyl-3-fluoro-9H-imidazo[1,5-a][1,2,4]triazolo[1,5-d][1,4]benzodiazepine (20 mg, 0.08 mmol), instead of phenylacetylene using 1-chloro-3-iodo-benzene instead of 3-chloro-10-iodo-9H-imidazo[1,5-a][1,2,4]triazolo[1,5-d][1,4]benzodiazepine, was converted to the title compound (SiO$_2$, hexane:ethyl acetate=90:10 to 0:100, 23 mg, 73%) which was obtained as a light brown solid. MS: m/e=376.3 [M+H]$^+$.

EXAMPLE 33

3-Fluoro-10-(3-trifluoromethyl-phenylethynyl)-9H-imidazo[1,5-a][1,2,4]triazolo[1,5-d][1,4]benzodiazepine As described for example 30, 10-ethynyl-3-fluoro-9H-imidazo[1,5-a][1,2,4]triazolo[1,5-d][1,4]benzodiazepine (100 mg, 0.38 mmol), instead of phenylacetylene using 3-bromobenzotrifluoride instead of 3-chloro-10-iodo-9H-imidazo[1,5-a][1,2,4]triazolo[1,5-d][1,4]benzodiazepine, was converted to the title compound (SiO$_2$, hexane:ethyl acetate=90:10 to 33:67, 14 mg, 8%) which was obtained as a light brown solid. MS: m/e=410.3 [M+H]$^+$.

EXAMPLE 34

3-Fluoro-10-(3-methoxy-phenylethynyl)-9H-imidazo[1,5-a][1,2,4]triazolo[1,5-d][1,4]benzodiazepine As described for example 30, 3-chloro-10-iodo-9H-imidazo[1,5-a][1,2,4]triazolo[1,5-d][1,4]benzodiazepine (100 mg, 0.26 mmol), using 1-ethynyl-3-methoxy-benzene instead of phenylacetylene, was converted to the title compound (SiO$_2$, hexane:ethyl acetate=90:10 to 33:67, 78 mg, 69%) which was obtained as a light brown solid. MS: m/e=388.1 [M+H]$^+$.

EXAMPLE 35

3-Fluoro-10-(3-methyl-phenylethynyl)-9H-imidazo[1,5-a][1,2,4]triazolo[1,5-d][1,4]benzodiazepine As described for example 30, 10-ethynyl-3-fluoro-9H-imidazo[1,5-a][1,2,4]triazolo[1,5-d][1,4]benzodiazepine (100 mg, 0.38 mmol), instead of phenylacetylene using 3-iodotoluene instead of 3-chloro-10-iodo-9H-imidazo[1,5-a][1,2,4]triazolo[1,5-d][1,4]benzodiazepine, was converted to the title compound (SiO$_2$, hexane:ethyl acetate=90:10 to 33:67, 120 mg, 85%) which was obtained as a light yellow solid. MS: m/e=356.2 [M+H]$^+$.

EXAMPLE 36

3-Fluoro-10-(3-isopropyl-phenylethynyl)-9H-imidazo[1,5-a][1,2,4]triazolo[1,5-d][1,4]benzodiazepine As described for example 30, 10-ethynyl-3-fluoro-9H-imidazo[1,5-a][1,2,4]triazolo[1,5-d][1,4]benzodiazepine (100 mg, 0.38 mmol), instead of phenylacetylene using 1-bromo-3-isopropylbenzene instead of 3-chloro-10-iodo-9H-imidazo[1,5-a][1,2,4]triazolo[1,5-d][1,4]benzodiazepine, was converted to the title compound (SiO$_2$, hexane:ethyl acetate=90: 10 to 33:67, 15 mg, 16%) which was obtained as a light brown semisolid. MS: m/e=384.2 [M+H]$^+$.

EXAMPLE 37

3-Fluoro-10-phenyl-9H-imidazo[1,5-a][1,2,4]triazolo[1,5-d][1,4]benzodiazepine

To a solution of 3-fluoro-10-(3-chloro-phenyl)-9H-imidazo[1,5-a][1,2,4]triazolo[1,5-d][1,4]benzodiazepine (1.00 g, 2.84 mmol) in acetic acid (100 mL) were added sodium acetate (852 mg, 10.4 mmol) and palladium(0) (5% on activated carbon, 100 mg, 0.05 mmol). The resulting mixture was stirred for 4 d at ambient temperature under a hydrogen atmosphere, filtered over dicalite and was concentrated. The residue was dissolved in ethyl acetate and was washed with aqueous sodium hydrogencarbonate (sat.). Drying over sodium sulfate and recrystallisation from ethyl acetate afforded the title compound (550 mg, 61%) as a white crystalline solid. MS: m/e=318.1 [M+H]$^+$.

EXAMPLE 38

3-Fluoro-10-(3-chloro-phenyl)-9H-imidazo[1,5-a][1,2,4]triazolo[1,5-d][1,4]benzodiazepine To a suspension of 9-fluoro-6H-1,3,3a,6-tetraaza-benzo[e]azulen-5-one (4.40 g, 20 mmol) in chloroform (250 mL) were added N,N-dimethyl-p-toluidine (12 mL) and phosphorus oxychloride (5.7 mL, 60 mmol), and the resulting mixture was stirred for 20 h at 65° C. Further N,N-dimethyl-p-toluidine (1.2 mL) and phosphorus oxychloride (0.6 mL, 6.3 mmol) were added, and stirring was continued for 1 h at 65° C. After cooling to ambient temperature the reaction mixture was poured onto aqueous sodium hydrogencarbonate (sat., 1 L), and the resulting mixture was stirred vigorously for 45 min. The layers were separated and the aqueous layers was extracted with chloroform. The combined organic layers were dried over magnesium sulfate and concentrated. Purification by chromatography (SiO$_2$, hexane:ethyl acetate=100:0 to 40:60) and recrystallisation from diisopropyl ether afforded 5-chloro-9-fluoro-4H-1,3,3a,6-tetraaza-benzo[e]azulene (3.85 g) as a brown solid which was dissolved in DMF (65 mL) and cooled to −55° C. 1-Chloro-3-isocyanomethyl-benzene (4.00 g, 26.4 mmol), and a solution of potassium tert-butylate (3.15 g, 27.3 mmol) in DMF (15 mL) were added at −50° C. to −55° C. The reaction mixture was stirred for 1 h at −40° C. to −50° C. before allowing to warm to ambient temperature. Acetic acid (1.1 mL) was added, and the mixture was poured onto aqueous sodium hydrogencarbonate (sat., 2 L) and extracted with ethyl acetate. The combined organic layers were washed with aqueous sodium hydrogen-carbonate (sat.) and dried over sodium sulfate. Purification by chromatography (SiO$_2$, dichloromethane:ethanol=100:0 to 98.5:1.5) afforded the title compound (1.25 g, 18%) as a white crystalline solid. MS: m/e=352.2 [M+H]$^+$.

EXAMPLE 39

3-Chloro-10-(6-methyl-pyridin-2-yl)-9H-imidazo[1,5-a][1,2,4]triazolo[1,5-d][1,4]benzodiazepine To a suspension of 3-chloro-10-iodo-9H-imidazo[1,5-a][1,2,4]triazolo[1,5-d][1,4]benzodiazepine (170 mg, 0.44 mmol) in DMF (2 mL) were added 6-methyl-2-pyridylzinc bromide (0.5 M in THF, 1.06 mL, 0.53 mmol) and tetrakis(triphenylphosphine)palladium(0) (10 mg, 0.01 mmol). The reaction mixture was stirred for 18 h at 60° C. Further tetrakis(triphenylphosphine)palladium(0) (10 mg, 0.01 mmol) was added, and stirring was continued for 24 h at 120° C. It was diluted with aqueous sodium carbonate (sat.) and extracted with dichloromethane. Drying over sodium sulfate and purification by chromatography (SiO$_2$, heptane:ethyl acetate:dichloromethane=20:30:50 to 0:90:10) afforded the title compound (53 mg, 34%) as a white solid. MS: m/e=349.3 [M+H]$^+$.

EXAMPLE 40

10-(2,2-Difluoro-vinyl)-9H-imidazo[1,5-a][1,2,4]triazolo[1,5-d][1,4]benzodiazepine Triphenylphosphine (525 mg, 2.00 mmol) was dissolved in dry DMF (2 ml) at ambient temperature. Dibromodifluoromethane (195 µl, 2.00 mmol) was added while a mildly exothermic reaction occured. After stirring for 30 min, 9H-imidazo[1,5-a][1,2,4]triazolo[1,5-d][1,4]benzodiazepine-10-carbaldehyde (251 mg, 1.00 mmol) was added followed by zinc dust (131 mg, 2.00 mmol). The resulting dark brown mixture was stirred for 1 h. It was poured onto aqueous sodium carbonate (saturated, 20 ml) and extracted with ethyl acetate. The combined organic layers were washed with brine, dried over sodium sulfate and were evaporated. Purification by chromatography (SiO$_2$, heptane:ethyl acetate:dichloromethane:methanol=75:15:10:0 to 0:80:10:10) afforded the title compound (121 mg, 42%) as a white solid. MS: m/e=286.02 [M+H]$^+$.

EXAMPLE 41

10-(2,2-Difluoro-ethyl)-9H-imidazo[1,5-a][1,2,4]triazolo[1,5-d][1,4]benzodiazepine As described for example 6, 10-(2,2-difluoro-vinyl)-9H-imidazo[1,5-a][1,2,4]triazolo[1,5-d][1,4]benzodiazepine (80 mg, 0.28 mmol), instead of 10-vinyl-9H-imidazo[1,5-a][1,2,4]triazolo[1,5-d][1,4]benzodiazepine, was converted to the title compound (SiO$_2$, heptane:ethyl acetate:dichloromethane:methanol=75:15:10:0 to 0:70:10:20, 31 mg, 39%) which was obtained as a white solid. MS: m/e=288.1 [M+H]$^+$.

EXAMPLE 42

3-Bromo-10-propyl-9H-imidazo[1,5-a][1,2,4]triazolo[1,5-d][1,4]benzodiazepine

As described for example 2c, 1-[3-bromo-9H-imidazo[1,5-a][1,2,4]triazolo[1,5-d][1,4]benzodiazepin-10-yl]-propan- 1-one (102 mg, 0.28 mmol), instead of 3-fluoro-9H-imidazo[1,5-a][1,2,4]triazolo[1,5-d][1,4]benzodiazepine-10-carbaldehyde, was converted to the title compound (32 mg, 32%) which was obtained as an off-white solid. MS: m/e=343.9/346.0 [M+H]$^+$.

EXAMPLE 43

3,6,10-Trimethyl-9H-imidazo[1,5-a][1,2,4]triazolo[1,5-d][1,4]benzodiazepine a) 5-Methyl-2-(4-methyl-imidazol-1-yl)-benzonitrile In analogy to example 5a, 2-fluoro-5-methyl-benzonitrile was reacted with 4-methylimidazole and potassium carbonate for 16 h at 90° C. After aqueous workup the title compound was obtained as a white solid (yield: 48%). MS: m/e=198.4 [M+H]$^+$.

b) 2-(5-Dimethylaminomethyl-4-methyl-imidazol-1-yl)-5-methyl-benzonitrile

In analogy to example 5b, 5-methyl-2-(4-methyl-imidazol-1-yl)-benzonitrile was reacted with Eschenmoser's salt in DMF for 4 h at 90° C. Evaporation of the solvent, aqueous workup and chromatography afforded the title compound as an oil that solidifies on standing (yield: 64%). MS: m/e=255.2 [M+H]$^+$.

c) [3-(2-Cyano-4-methyl-phenyl)-5-methyl-3H-imidazol-4-ylmethyl]-trimethyl-ammonium; iodide In analogy to example 5c, 2-(5-dimethylaminomethyl-4-methyl-imidazol-1-yl)-5-methyl-benzonitrile was reacted with methyl iodide for 7 days at 4° C. The title compound was obtained as a white crystalline material (yield: 83%). MS: m/e=269.5 [M]$^+$.

d) 3,6,10-Trimethyl-9H-imidazo[1,5-a][1,2,4]triazolo[1,5-d][1,4]benzodiazepine

In analogy to example 5d, 3-(2-cyano-4-methyl-phenyl)-5-methyl-3H-imidazol-4-ylmethyl]-trimethyl-ammonium; iodide was reacted with acetic hydrazide in DMF for 24 h at 150° C. Evaporation of the solvent and trituration with MeOH afforded the title compound as a white solid (yield: 9%). MS: m/e=266.4 [M+H]$^+$.

EXAMPLE 44

3,10-Dimethyl-9H-imidazo[1,5-a][1,2,4]triazolo[1,5-d][1,4]benzodiazepine

In analogy to example 5d, 3-(2-cyano-4-methyl-phenyl)-5-methyl-3H-imidazol-4-ylmethyl]-trimethyl-ammonium; iodide (example 43c) was reacted with formic hydrazide in DMF for 24 h at 150° C. Evaporation of the solvent and trituration with MeOH afforded the title compound as a white solid (yield: 14%). MS: m/e=252.2 [M+H]$^+$.

EXAMPLE 45

3-Methoxy-6,10-dimethyl-9H-imidazo[1,5-a][1,2,4]triazolo[1,5-d][1,4]benzodiazepine a) 5-Methoxy-2-(4-methyl-imidazol-1-yl)-benzonitrile In analogy to example 5a, 2-fluoro-5-methoxy-benzonitrile was reacted with 4-methylimidazole and potassium carbonate for 48 h at 100° C. After aqueous workup and crystallization from Ethyl acetate/diisopropylether the title compound was obtained as a white solid (yield: 72%). MS: m/e=214.1 [M+H]$^+$.

b) 2-(5-Dimethylaminomethyl-4-methyl-imidazol-1-yl)-5-methoxy-benzonitrile

In analogy to example 5b, 5-methoxy-2-(4-methyl-imidazol-1-yl)-benzonitrile was reacted with Eschenmoser's salt in DMF for 16 h at 70° C. Evaporation of the solvent, aqueous workup and chromatography afforded the title compound as an oil (yield: 83%). MS: m/e=271.4 [M+H]$^+$.

c) [3-(2-Cyano-4-methoxy-phenyl)-5-methyl-3H-imidazol-4-ylmethyl]-trimethyl-ammonium; iodide In analogy to example 5c, 2-(5-dimethylaminomethyl-4-methyl-imidazol-1-yl)-5-methoxy-benzonitrile was reacted with methyl iodide for 6 days at 4° C. The title compound was obtained as a white crystalline material (yield: 89%). MS: m/e=285.1 [M]$^+$.

d) 3-Methoxy-6,10-dimethyl-9H-imidazo[1,5-a][1,2,4]triazolo[1,5-d][1,4]benzodiazepine In analogy to example 5d, [3-(2-cyano-4-methoxy-phenyl)-5-methyl-3H-imidazol-4-ylmethyl]-trimethyl-ammonium; iodide was reacted with acetic hydrazide in DMF for 24 h at 150° C. Evaporation of the solvent and trituration with MeOH afforded the title compound as a white solid (yield: 17%). MS: m/e=282.4 [M+H]$^+$.

EXAMPLE 46

3-Methoxy-10-methyl-9H-imidazo[1,5-a][1,2,4]triazolo[1,5-d][1,4]benzodiazepine

In analogy to example 5d, [3-(2-cyano-4-methoxy-phenyl)-5-methyl-3H-imidazol-4-ylmethyl]-trimethyl-ammonium; iodide (example 45c) was reacted with formic hydrazide in DMF for 24 h at 150° C. Evaporation of the solvent and trituration with MeOH afforded the title compound as a white solid (yield: 29%). MS: m/e=268.4 [M+H]$^+$.

EXAMPLE 47

3-Trifluoromethyl-10-methyl-9H-imidazo[1,5-a][1,2,4]triazolo[1,5-d][1,4]benzodiazepine a) 5-Trifluoromethyl-2-(4-methyl-imidazol-1-yl)-benzonitrile In analogy to example 5a, 2-fluoro-5-(trifluoromethyl)-benzonitrile was reacted with 4-methylimidazole and potassium carbonate for 16 h at 90° C. After aqueous workup and extraction with Ethyl acetate, the organic phase was dried (Na$_2$SO$_4$) and concentrated to furnish a 3.4:1 mixture of the title compound and its regioisomer [5-trifluoromethyl-2-(5-methyl-imidazol-1-yl)-benzonitrile] as a light brown oil (yield: 85%). MS: m/e=252.3 [M+H]$^+$.

b) 5-Trifluoromethyl-2-(5-dimethylaminomethyl-4-methyl-imidazol-1-yl)-benzonitrile In analogy to example 5b, 5-trifluoromethyl-2-(4-methyl-imidazol-1-yl)-benzonitrile (+regioisomer) was reacted with Eschenmoser's salt in DMF for 16 h at 90° C. Evaporation of the solvent, aqueous workup and chromatography afforded the title compound as a yellow oil that was sufficiently pure to be used in the next step (yield: 53%). MS: m/e=309.3 [M+H]$^+$.

c) [3-(2-Cyano-4-trifluoromethyl-phenyl)-5-methyl-3H-imidazol-4-ylmethyl]-trimethyl-ammonium; iodide In analogy to example 5c, 5-trifluoromethyl-2-(5-dimethylaminomethyl-4-methyl-imidazol-1-yl)-benzonitrile was reacted with methyl iodide for 3 days at 4° C. The title compound was obtained as a white crystalline material (yield: 61%). MS: m/e=323.3 [M]+.

d) 3-Trifluoromethyl-10-methyl-9H-imidazo[1,5-a][1,2,4]triazolo[1,5-d][1,4]benzodiazepine In analogy to example 5d, [3-(2-cyano-4-trifluoromethyl-phenyl)-5-methyl-3H-imidazol-4-ylmethyl]-trimethyl-ammonium; iodide was reacted with formic hydrazide in DMF for 16 h at 150° C. Evaporation of the solvent and chromatography (SiO$_2$, dichloromethane:methanol=100:0 to 97:3) afforded the title compound (yield: 44%) as an off-white solid. MS: m/e=306.1 [M+H]+.

EXAMPLE 48

10-Methyl-3-nitro-9H-imidazo[1,5-a][1,2,4]triazolo[1,5-d][1,4]benzodiazepine a) 2-(4-Methyl-imidazol-1-yl)-5-nitro-benzonitrile In analogy to example 5a, 2-fluoro-5-nitro-benzonitrile was reacted with 4-methylimidazole and potassium carbonate for 1 h at 20° C. Aqueous workup afforded a 3.6:1 mixture of the title compound and its regioisomer [2-(5-methyl-imidazol-1-yl)-5-nitro-benzonitrile] as a light brown solid (yield: 69%). MS: m/e=229.4 [M+H]+.

b) 2-(5-Dimethylaminomethyl-4-methyl-imidazol-1-yl)-5-nitro-benzonitrile

In analogy to example 5b, 2-(4-methyl-imidazol-1-yl)-5-nitro-benzonitrile (+regioisomer) was reacted with Eschenmoser's salt in DMF for 16 h at 90° C. Evaporation of the solvent, aqueous workup and chromatography afforded the title compound as a yellow oil that was sufficiently pure to be used in the next step (yield: 35%). MS: m/e=286.1 [M+H]+.

c) [3-(2-Cyano-4-nitro-phenyl)-5-methyl-3H-imidazol-4-ylmethyl]-trimethyl-ammonium; iodide In analogy to example 5c, 2-(5-dimethylaminomethyl-4-methyl-imidazol-1-yl)-5-nitro-benzonitrile was reacted with methyl iodide for 3 days at 4° C. The title compound was obtained as a light brown crystalline material which was sufficiently pure to be used in the next step (yield: 75%). MS: m/e=241.4 [M-NMe$_3$]+.

d) 10-Methyl-3-nitro-9H-imidazo[1,5-a][1,2,4]triazolo[1,5-d][1,4]benzodiazepine

In analogy to example 5d, [3-(2-cyano-4-nitro-phenyl)-5-methyl-3H-imidazol-4-ylmethyl]-trimethyl-ammonium; iodide was reacted with formic hydrazide in DMF for 16 h at 150° C. Evaporation of the solvent and chromatography (SiO$_2$, dichloromethane:methanol=100:0 to 97:3) afforded the title compound (yield: 12%) as an off-white solid. MS: m/e=283.1 [M+H]+.

EXAMPLE 49

3-Trifluoromethoxy-10-methyl-9H-imidazo[1,5-a][1,2,4]triazolo[1,5-d][1,4]benzodiazepine a) 2-Fluoro-5-trifluoromethoxy-benzaldehyde A solution of 1-fluoro-4-trifluoromethoxy-benzene (21.0 g, 117 mmol) in THF (233 ml) was cooled to <−70° C. Tert.-butyllithium (86 ml of a 1.5 molar solution in pentane, 129 mmol) was added at such a rate that temperature was kept <−70° C. Stirring in the dry ice bath was continued for 15 min, then DMF (11.6 ml, 150 mmol) was added dropwise keeping temperature <−70° C. After 30 min the reaction mixture was allowed to reach rt, quenched with saturated NH$_4$Cl solution and extracted with ether. The organic phase was washed with brine, concentrated and chromatographed (SiO$_2$, heptane: ethyl acetate=100:0 to 80:2). The title compound (11.0 g, 53%) was obtained as a light yellow oil. $^1$H-NMR (300 MHz, DMSO): δ=7.60 (t, J=9.2 Hz, 1H), 7.75-7.85 (m, 2H), 10.20 (s, 1H).

b) E-2-Fluoro-5-trifluoromethoxy-benzaldehyde oxime

A solution of 2-fluoro-5-trifluoromethoxy-benzaldehyde (9.78 g, 47 mmol) in ethanol (50 ml) was treated with hydroxylamine HCl (3.59 g, 52 mmol) and sodium acetate (4.27 g, 52 mmol). The mixture was refluxed for 2 h, the solvent was evaporated and the residue stirred with water (50 ml). The precipitate was filtered, dried and chromatographed (SiO$_2$, heptanes:Ethyl acetate=100:0 to 80:2) and afforded the title compound (9.21 g, 88%) as a white solid. MS: m/e=223.0 [M]+.

c) 2-Fluoro-5-trifluoromethoxy-benzonitrile

To a solution of E-2-fluoro-5-trifluoromethoxy-benzaldehyde oxime (47.5 g, 213 mmol) in THF (400 ml) was added triethylamine (65.0 ml, 466 mmol). The mixture was cooled in an ice bath and trifluoroacetic anhydride (32.8 ml, 236 mmol) was added at such a rate that the temperature was kept <30° C. After 1 h at rt all volatiles were evaporated (40° C., 200 mbar). The oily residue was partitioned (ether/water), the organic phase was dried (Na$_2$SO$_4$) and concentrated. Distillation (24 mbar, T=80-83° C.) afforded the title compound (36.1 g, 83%) that was sufficiently pure to be used in the next step. MS: m/e=205 [M]+.

d) 5-Trifluoromethoxy-2-(4-methyl-imidazol-1-yl)-benzonitrile

In analogy to example 5a, 2-fluoro-5-trifluoromethoxy-benzonitrile was reacted with 4-methylimidazole and potassium carbonate for 16 h at 90° C. Aqueous workup afforded a 3:1 mixture of the title compound and its regioisomer [5-trifluoromethoxy-2-(5-methyl-imidazol-1-yl)-benzonitrile] as a light brown viscous oil (yield: 100%). $^1$H-NMR (300 MHz, DMSO): δ=2.19 (s, 3H), 7.37 (s, 1H), 7.75-7.90 (m, 2H), 8.02 (s, 1H), 8.27 (d, J=2.7 Hz, 1H).

e) 2-(5-Dimethylaminomethyl-4-methyl-imidazol-1-yl)-5-trifluoromethoxy-benzonitrile In analogy to example 5b, 5-trifluoromethoxy-2-(4-methyl-imidazol-1-yl)-benzonitrile (+regioisomer) was reacted with Eschenmoser's salt in DMF for 24 h at 90° C. Evaporation of the solvent, aqueous workup and chromatography afforded the title compound as a colorless oil that was sufficiently pure to be used in the next step (yield: 38%). $^1$H-NMR (300 MHz, DMSO): δ=1.93 (s, 6H), 2.17 (s, 3H), 3.21 (s, 2H), 7.80-7.95 (m, 3H), 8.22 (s, 1H).

f) [3-(2-Cyano-4-trifluoromethoxy-phenyl)-5-methyl-3H-imidazol-4-ylmethyl]-trimethyl-ammonium; iodide In analogy to example 5c, 2-(5-dimethylaminomethyl-4-methyl-imidazol-1-yl)-5-trifluoromethoxy-benzonitrile was reacted with methyl iodide for 2 days at 4° C. The title compound was obtained as a white crystalline material (yield: 53%). MS: m/e=339.1 [M]+.

g) 3-Trifluoromethoxy-10-methyl-9H-imidazo[1,5-a][1,2,4]triazolo[1,5-d][1,4]benzodiazepine In analogy to example 5d, [3-(2-cyano-4-trifluoromethoxy-phenyl)-5-methyl-3H-imidazol-4-ylmethyl]-trimethyl-ammonium; iodide was reacted with formic hydrazide in DMF for 4 h at 120° C., then for 16 h at 150° C. Evaporation of the solvent and chromatography (SiO$_2$, dichloromethane:methanol=100:0 to 96:4) afforded the title compound (yield: 39%) as a white solid. MS: m/e=322.3 [M+H]$^+$.

EXAMPLE 50

3-Chloro-6,10-dimethyl-9H-imidazo[1,5-a][1,2,4]triazolo[1,5-d][1,4]benzodiazepine a) 5-Chloro-2-(4-methyl-imidazol-1-yl)-benzonitrile In analogy to example 5a, 5-chloro-2-fluoro-benzonitrile was reacted with 4-methylimidazole and potassium carbonate for 20 h at 90° C. After aqueous workup and crystallization from Ethyl acetate the title compound was obtained as a white solid (yield: 63%). MS: m/e=218.2 [M+H]$^+$.

b) 5-Chloro-2-(5-dimethylaminomethyl-4-methyl-imidazol-1-yl)-benzonitrile

In analogy to example 5b, 5-chloro-2-(4-methyl-imidazol-1-yl)-benzonitrile was reacted with Eschenmoser's salt in DMF for 16 h at 90° C. Evaporation of the solvent, aqueous workup and crystallization from Ethyl acetate afforded the title compound as a white solid (yield: 17%). MS: m/e=275.1 [M+H]$^+$.

c) [3-(4-Chloro-2-cyano-phenyl)-5-methyl-3H-imidazol-4-ylmethyl]-trimethyl-ammonium; iodide In analogy to example 5c, 5-chloro-2-(5-dimethylaminomethyl-4-methyl-imidazol-1-yl)-benzonitrile was reacted with methyl iodide for 4 days at 4° C. The title compound was obtained as a white crystalline material (yield: 94%). MS: m/e=230.2 [M-NMe$_3$]$^+$.

d) 3-Chloro-6,10-dimethyl-9H-imidazo[1,5-a][1,2,4]triazolo[1,5-d][1,4]benzodiazepine In analogy to example 5d, [3-(4-chloro-2-cyano-phenyl)-5-methyl-3H-imidazol-4-ylmethyl]-trimethyl-ammonium; iodide was reacted with acetic hydrazide in DMF for 24 h at 150° C. On cooling in an ice bath the title compound crystallized as a white solid (yield: 43%). MS: m/e=282.4 [M+H]$^+$.

EXAMPLE 51

3-Fluoro-6,10-dimethyl-9H-imidazo[1,5-a][1,2,4]triazolo[1,5-d][1,4]benzodiazepine a) 5-Fluoro-2-(4-methyl-imidazol-1-yl)-benzonitrile In analogy to example 5a, 2,5-difluoro-benzonitrile was reacted with 4-methylimidazole and potassium carbonate for 20 h at 90° C. After aqueous workup and crystallization from Ethyl acetate the title compound was obtained as a white solid (yield: 41%). MS: m/e=202.3 [M+H]$^+$.

b) 2-(5-Dimethylaminomethyl-4-methyl-imidazol-1-yl)-5-fluoro-benzonitrile

In analogy to example 5b, 5-fluoro-2-(4-methyl-imidazol-1-yl)-benzonitrile was reacted with Eschenmoser's salt in DMF for 24 h at 90° C. Evaporation of the solvent, aqueous workup and crystallization from Ethyl acetate/diisopropylether afforded the title compound as a white solid (yield: 34%). MS: m/e=259.2 [M+H]$^+$.

c) [3-(2-Cyano-4-fluoro-phenyl)-5-methyl-3H-imidazol-4-ylmethyl]-trimethyl-ammonium; iodide In analogy to example 5c, 2-(5-dimethylaminomethyl-4-methyl-imidazol-1-yl)-5-fluoro-benzonitrile was reacted with methyl iodide for 4 days at 4° C. The title compound was obtained as a white crystalline material (yield: 98%). MS: m/e=214.1 [M-NMe$_3$]$^+$.

d) 3-Fluoro-6,10-dimethyl-9H-imidazo[1,5-a][1,2,4]triazolo[1,5-d][1,4]benzodiazepine In analogy to example 5d, [3-(2-cyano-4-fluoro-phenyl)-5-methyl-3H-imidazol-4-ylmethyl]-trimethyl-ammonium; iodide was reacted with acetic hydrazide in DMF for 24 h at 150° C. The solvent was evaporated and the residue was crystallized from MeOH to afford the title compound as a white solid (yield: 28%). MS: m/e=270.3 [M+H]$^+$.

EXAMPLE 52

3-Iodo-6,10-dimethyl-9H-imidazo[1,5-a][1,2,4]triazolo[1,5-d][1,4]benzodiazepine a) 5-Iodo-2-(4-methyl-imidazol-1-yl)-benzonitrile In analogy to example 5a, 2-fluoro-5-iodo-benzonitrile was reacted with 4-methylimidazole and potassium carbonate for 20 h at 90° C. Aqueous workup afforded a 1.9:1 mixture of the title compound and its regioisomer [5-iodo-2-(5-methyl-imidazol-1-yl)-benzonitrile] as a white solid (yield: 92%). MS: m/e=310.1 [M+H]$^+$.

b) 2-(5-Dimethylaminomethyl-4-methyl-imidazol-1-yl)-5-iodo-benzonitrile

In analogy to example 5b, 5-iodo-2-(4-methyl-imidazol-1-yl)-benzonitrile (+regioisomer) was reacted with Eschenmoser's salt in DMF for 72 h at 90° C. Evaporation of the solvent, aqueous workup and chromatography (SiO$_2$, dichloromethane:methanol=100:0 to 97:3) afforded the title compound as a white solid (yield: 38%). MS: m/e=367.0 [M+H]$^+$.

c) [3-(2-Cyano-4-iodo-phenyl)-5-methyl-3H-imidazol-4-ylmethyl]-trimethyl-ammonium; iodide In analogy to example 5c, 2-(5-dimethylaminomethyl-4-methyl-imidazol-1-yl)-5-iodo-benzonitrile was reacted with methyl iodide for 3 days at 4° C. The title compound was obtained as a white crystalline material (yield: 94%). MS: m/e=322.1 [M-NMe$_3$]$^+$.

d) 3-Iodo-6,10-dimethyl-9H-imidazo[1,5-a][1,2,4]triazolo[1,5-d][1,4]benzodiazepine In analogy to example 5d, [3-(2-cyano-4-iodo-phenyl)-5-methyl-3H-imidazol-4-ylmethyl]-trimethyl-ammonium; iodide was reacted with acetic hydrazide in DMF for 24 h at 150° C. On cooling in an ice bath the title compound crystallized as an off-white solid (yield: 29%). MS: m/e=378.1 [M+H]$^+$.

EXAMPLE 53

3-Iodo-10-methyl-9H-imidazo[1,5-a][1,2,4]triazolo[1,5-d][1,4]benzodiazepine hydrochloride (1:1)

In analogy to example 5d, [3-(2-cyano-4-iodo-phenyl)-5-methyl-3H-imidazol-4-ylmethyl]-trimethyl-ammonium; iodide (example 52c) was reacted with formic hydrazide in DMF for 24 h at 150° C. Evaporation of the solvent and trituration with MeOH gave the tide compound as a free base. Crystallization of the hydrochloride salt from MeOH/ether afforded the title compound as an off-white solid (yield: 43%). MS: m/e=364.0 [M+H]$^+$.

EXAMPLE 54

4-Chloro-3-fluoro-10-methyl-9H-imidazo[1,5-a][1,2,4]triazolo[1,5-d][1,4]benzodiazepine hydrochloride (1:1)

a) 2-Chloro-3-fluoro-6-(4-methyl-imidazol-1-yl)-benzonitrile

A solution of 2-chloro-3,6-difluoro-benzaldehyde (16.5 g, 93 mmol) in ethanol (80 ml) was treated with hydroxylamine HCl (7.80 g, 112 mmol) and sodium acetate (9.20 g, 112 mmol). The mixture was heated under reflux for 16 h, then the solvent was evaporated, and the residue stirred with water. The precipitate was filtered and dried to afford 2-chloro-3,6-difluoro-benzaldehyde oxime. It was dissolved in acetic anhydride (140 ml) and refluxed for 16 h, then the mixture was evaporated to afford 2-chloro-3,6-difluoro-benzonitrile as a light brown liquid (10.6 g, 65%). In analogy to example 5a, this compound was reacted with 4-methylimidazole and potassium carbonate for 20 h at 90° C. Aqueous workup, extraction with Ethyl acetate followed by chromatography (SiO$_2$, dichloromethane:methanol=100:0 to 97:3) afforded the title compound as a white solid (yield: 6%). MS: m/e=336.1 [M+H]$^+$.

b) 2-Chloro-6-(5-dimethylaminomethyl-4-methyl-imidazol-1-yl)-3-fluoro-benzonitrile In analogy to example 5b, 2-chloro-3-fluoro-6-(4-methyl-imidazol-1-yl)-benzonitrile was reacted with Eschenmoser's salt in DMF for 16 h at 90° C. Evaporation of the solvent, aqueous workup and chromatography (SiO$_2$, dichloromethane:methanol=100:0 to 97:3) afforded the title compound as a light yellow oil (yield: 52%). MS: m/e=293.1 [M+H]$^+$.

c) [3-(3-Chloro-2-cyano-4-fluoro-phenyl)-5-methyl-3H-imidazol-4-ylmethyl]-trimethyl-ammonium; iodide In analogy to example 5c, 2-chloro-6-(5-dimethylaminomethyl-4-methyl-imidazol-1-yl)-3-fluoro-benzonitrile was reacted with methyl iodide for 3 days at 4° C. The title compound was obtained as an off-white crystalline material (yield: 59%). MS: m/e=248.1 [M-NMe$_3$]$^+$.

d) 4-Chloro-3-fluoro-10-methyl-9H-imidazo[1,5-a][1,2,4]triazolo[1,5-d][1,4]benzodiazepine hydrochloride (1:1)

In analogy to example 5d, [3-(3-chloro-2-cyano-4-fluoro-phenyl)-5-methyl-3H-imidazol-4-ylmethyl]-trimethyl-ammonium; iodide was reacted with formic hydrazide in DMF for 16 h at 150° C. Evaporation of the solvent and chromatography (SiO$_2$, dichloromethane:methanol=100:0 to 97:3) afforded the free base of the title compound. Crystallization of the HCl-salt from MeOH/ether affords the title compound as an off-white solid (yield: 44%). MS: m/e=290.0 [M+H]$^+$.

EXAMPLE 55

6,10-Dimethyl-9H-imidazo[1,5-a][1,2,4]triazolo[1,5-d][1,4]benzodiazepine a) 2-(4-Methyl-imidazol-1-yl)-benzonitrile In analogy to example 5a, 2-fluoro-benzonitrile was reacted with 4-methylimidazole and potassium carbonate for 16 h at 90° C. After aqueous workup the title compound was obtained as a white solid (yield: 60%). MS: m/e=184.2 [M+H]$^+$.

b) 2-(5-Dimethylaminomethyl-4-methyl-imidazol-1-yl)-benzonitrile

In analogy to example 5b, 2-(4-methyl-imidazol-1-yl)-benzonitrile was reacted with Eschenmoser's salt in DMF for 5 h at 90° C. Evaporation of the solvent, aqueous workup and chromatography (SiO$_2$, dichloromethane:methanol=100:0 to 96:4) afforded the title compound as a light yellow oil (yield: 57%). MS: m/e=241.4 [M+H]$^+$.

c) [3-(2-Cyano-phenyl)-5-methyl-3H-imidazol-4-ylmethyl]-trimethyl-ammonium; iodide In analogy to example 5c, 2-(5-dimethylaminomethyl-4-methyl-imidazol-1-yl)-benzonitrile was reacted with methyl iodide for 2 days at 4° C. The title compound was obtained as a white crystalline material (yield: 98%). MS: m/e=196.1 [M-NMe$_3$]$^+$.

d) 6,10-Dimethyl-9H-imidazo[1,5-a][1,2,4]triazolo[1,5-d][1,4]benzodiazepine

In analogy to example 5d, [3-(2-cyano-phenyl)-5-methyl-3H-imidazol-4-ylmethyl]-trimethyl-ammonium; iodide was reacted with acetic hydrazide in DMF for 24 h at 150° C. Evaporation of the solvent and chromatography (SiO$_2$, dichloromethane:methanol=100:0 to 97:3) afforded the title compound as an off-white solid (yield: 10%). MS: m/e=252.3 [M+H]$^+$.

EXAMPLE 56

4-Fluoro-6,10-dimethyl-9H-imidazo[1,5-a][1,2,4]triazolo[1,5-d][1,4]benzodiazepine a) 2-Fluoro-6-(4-methyl-imidazol-1-yl)-benzonitrile In analogy to example 5a, 2,6-difluoro-benzonitrile was reacted with 4-methylimidazole and potassium carbonate for 16 h at 90° C. After extractive workup and chromatography (SiO$_2$, dichloromethane:methanol=100:0 to 98:2) the title compound was obtained as an off-white solid (yield: 29%). $^1$H-NMR (300 MHz, DMSO): δ=2.19 (d, J=0.8 Hz, 3H), 7.39 (s with fine splitting, 1H), 7.56-7.64 (m, 2H), 7.92 (mc, 1H), 8.04 (d, J=1.2 Hz, 1H).

b) 2-(5-Dimethylaminomethyl-4-methyl-imidazol-1-yl)-6-fluoro-benzonitrile

In analogy to example 5b, 2-fluoro-6-(4-methyl-imidazol-1-yl)-benzonitrile was reacted with Eschenmoser's salt in DMF for 7 h at 90° C. Evaporation of the solvent, extractive workup and chromatography (SiO$_2$, dichloromethane:methanol=100:0 to 97:3) furnished the title compound as a light yellow solid (yield: 46%). $^1$H-NMR (400 MHz, DMSO): δ=1.94 (s, 6H), 2.17 (s, 3H), 3.23 (s, 2H), 7.61-7.67 (m, 2H), 7.86 (s, 1H), 7.86-7.96 (m, 1H).

c) [3-(2-Cyano-3-fluoro-phenyl)-5-methyl-3H-imidazol-4-ylmethyl]-trimethyl-ammonium; iodide In analogy to example 5c, 2-(5-dimethylaminomethyl-4-methyl-imidazol-1-yl)-6-fluoro-benzonitrile was reacted with methyl iodide for 2 days at 4° C. The title compound was obtained as a white crystalline material (yield: 98%). MS: m/e=214.3 [M-NMe$_3$]$^+$.

d) 4-Fluoro-6,10-dimethyl-9H-imidazo[1,5-a][1,2,4]triazolo[1,5-d][1,4]benzodiazepine In analogy to example 5d, [3-(2-cyano-3-fluoro-phenyl)-5-methyl-3H-imidazol-4-ylmethyl]-trimethyl-ammonium; iodide was reacted with acetic hydrazide in DMF for 24 h at 150° C. The solvent was evaporated and the residue was crystallized from MeOH to afford the title compound as an off-white solid (yield: 35%). MS: m/e=270.3 [M+H]$^+$.

EXAMPLE 57

4-Fluoro-10-methyl-9H-imidazo[1,5-a][1,2,4]triazolo[1,5-d][1,4]benzodiazepine In analogy to example 5d, [3-(2-cyano-3-fluoro-phenyl)-5-methyl-3H-imidazol-4-ylmethyl]-trimethyl-ammonium; iodide (example 56c) was reacted with formic hydrazide in DMF for 24 h at 150° C. The solvent was evaporated and the residue was crystallized from MeOH to afford the title compound as an off-white solid (yield: 27%). MS: m/e=256.2 [M+H]$^+$.

EXAMPLE 58

4-Chloro-6,10-dimethyl-9H-imidazo[1,5-a][1,2,4]triazolo[1,5-d][1,4]benzodiazepine a) 2-Chloro-6-(4-methyl-imidazol-1-yl)-benzonitrile In analogy to example 5a, 2-chloro-6-fluoro-benzonitrile was reacted with 4-methylimidazole and potassium carbonate for 16 h at 90° C. After aqueous workup and crystallization from Ethyl acetate/diisopropylether the title compound was obtained as an off-white solid (yield: 73%). MS: m/e=218.2 [M+H]$^+$.

b) 2-Chloro-6-(5-dimethylaminomethyl-4-methyl-imidazol-1-yl)-benzonitrile

In analogy to example 5b, 2-chloro-6-(4-methyl-imidazol-1-yl)-benzonitrile was reacted with Eschenmoser's salt in DMF for 5 h at 90° C. Evaporation of the solvent, extractive workup and chromatography (SiO$_2$, dichloromethane:methanol=100:0 to 98:2) afforded the title compound as a white solid (yield: 29%). MS: m/e=275.1 [M+H]$^+$.

c) [3-(3-Chloro-2-cyano-phenyl)-5-methyl-3H-imidazol-4-ylmethyl]-trimethyl-ammonium; iodide In analogy to example 5c, 2-chloro-6-(5-dimethylaminomethyl-4-methyl-imidazol-1-yl)-benzonitrile was reacted with methyl iodide for 2 days at 4° C. The title compound was obtained as a white crystalline material (yield: 88%). MS: m/e=230.3 [M-NMe$_3$]$^+$.

d) 4-Chloro-6,10-dimethyl-9H-imidazo[1,5-a][1,2,4]triazolo[1,5-d][1,4]benzodiazepine In analogy to example 5d, [3-(3-chloro-2-cyano-phenyl)-5-methyl-3H-imidazol-4-ylmethyl]-trimethyl-ammonium; iodide was reacted with acetic hydrazide in DMF for 24 h at 150° C. The solvent was evaporated and the residue was chromatographed (SiO$_2$, dichloromethane:methanol=100:0 to 97:3) to furnish the title compound as an off-white solid (yield: 43%). MS: m/e=286.1 [M+H]$^+$.

EXAMPLE 59

4-Chloro-10-methyl-9H-imidazo[1,5-a][1,2,4]triazolo[1,5-d][1,4]benzodiazepine In analogy to example 5d, [3-(3-chloro-2-cyano-phenyl)-5-methyl-3H-imidazol-4-ylmethyl]-trimethyl-ammonium; iodide (example 58c) was reacted with formic hydrazide in DMF for 24 h at 150° C. The solvent was evaporated and the residue was chromatographed (SiO$_2$, dichloromethane:methanol=100:0 to 97:3) to furnish the title compound as an off-white solid (yield: 37%). MS: m/e=272.2 [M+H]$^+$.

EXAMPLE 60

1-Fluoro-10-methyl-9H-imidazo[1,5-a][1,2,4]triazolo[1,5-d][1,4]benzodiazepine hydrochloride (1:1)

a) 3-Fluoro-2-(4-methyl-imidazol-1-yl)-benzonitrile

In analogy to example 5a, 2,3-difluoro-benzonitrile was reacted with 4-methylimidazole and potassium carbonate for 16 h at 90° C. After aqueous workup and crystallization from Ethyl acetate/diisopropylether the title compound was obtained as an off-white solid (yield: 28%). $^1$H-NMR (300 MHz, DMSO): δ=2.19 (d, J=0.9 Hz, 3H), 7.26 (s with fine splitting, 1H), 7.71-7.89 (m, 1H), 7.86-7.94 (m, 3H)

b) 2-(5-Dimethylaminomethyl-4-methyl-imidazol-1-yl)-3-fluoro-benzonitrile

In analogy to example 5b, 3-fluoro-2-(4-methyl-imidazol-1-yl)-benzonitrile was reacted with Eschenmoser's salt in DMF for 16 h at 90° C. Evaporation of the solvent, aqueous workup and chromatography (SiO$_2$, dichloromethane:methanol=100:0 to 98:2) afforded the title compound as a light yellow oil (yield: 13%). $^1$H-NMR (400 MHz, DMSO): δ=1.91 (s, 6H), 2.17 (s, 3H), 3.17 (s, 2H), 7.72-7.92 (m, 4H)

c) [3-(2-Cyano-6-fluoro-phenyl)-5-methyl-3H-imidazol-4-ylmethyl]-trimethyl-ammonium; iodide In analogy to example 5c, 2-(5-dimethylaminomethyl-4-methyl-imidazol-1-yl)-3-fluoro-benzonitrile was reacted with methyl iodide for 2 days at 4° C. The title compound was obtained as a white crystalline material (yield: 92%). MS: m/e=214.2 [M-NMe$_3$]$^+$.

d) 1-Fluoro-10-methyl-9H-imidazo[1,5-a][1,2,4]triazolo[1,5-d][1,4]benzodiazepine hydrochloride (1:1)

In analogy to example 5d, [3-(2-cyano-6-fluoro-phenyl)-5-methyl-3H-imidazol-4-ylmethyl]-trimethyl-ammonium; iodide was reacted with formic hydrazide in DMF for 16 h at 150° C. Evaporation of the solvent, aqueous workup and chromatography (SiO$_2$, dichloromethane:methanol=100:0 to 97:3) funished the title compound as a free base. The hydrochloride salt was crystallized from MeOH/ether (overall yield: 5%). MS: m/e=256.3 [M+H]$^+$.

The invention claimed is:
1. A compound of formula I

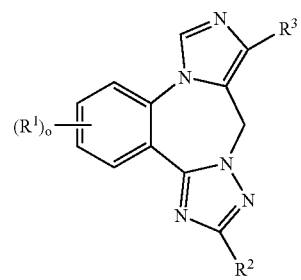

wherein
R$^1$ is hydrogen, halogen, lower alkyl, lower alkyl substituted by halogen, lower alkoxy, lower alkoxy substituted by halogen, nitro, cycloalkyl, —O(CH$_2$)$_m$O(CH$_2$)$_m$OH or —C≡C—R';
R$^2$ is hydrogen or methyl;
R$^3$ is lower alkyl, lower alkyl substituted by halogen, lower alkenyl, lower alkenyl substituted by halogen, lower alkynyl, —(CH$_2$)$_n$-cycloalkyl, —(CR'R")$_m$—CH$_3$, phenyl that is unsubstituted or substituted by halogen, pyridinyl or thienyl each of which is unsubstituted or substituted by lower alkyl, —(CH$_2$)$_n$—NH-cycloalkyl, lower alkenyl-cycloalkyl, lower alkynyl-(CR'R")$_m$OH, or lower alkynyl-phenyl wherein the phenyl ring is unsubstituited or substituted by halogen, CF$_3$, lower alkyl or lower alkoxy;

R' is hydrogen or lower alkyl;
R" is hydrogen, hydroxy or lower alkyl;
n is 0, 1 or 2;
m is 1, 2 or 3; and
o is 1 or 2;

or a pharmaceutically acceptable acid addition salt thereof.

2. A compound of formula I in accordance with claim 1, wherein R$^3$ is lower alkyl.

3. A compound of formula I in accordance with claim 2, selected from the group consisting of 10-methyl-9H-imidazo[1,5-a][1,2,4]triazolo[1,5-d][1,4]benzodiazepine,
3-fluoro-10-methyl-9H-imidazo[1,5-a][1,2,4]triazolo[1,5-d][1,4]benzodiazepine,
3-chloro-10-methyl-9H-imidazo[1,5-a][1,2,4]triazolo[1,5-d][1,4]benzodiazepine,
10-ethyl-3-fluoro-9H-imidazo[1,5-a][1,2,4]triazolo[1,5-d][1,4]benzodiazepine,
3-chloro-10-ethyl-9H-imidazo[1,5-a][1,2,4]triazolo[1,5-d][1,4]benzodiazepine,
10-ethyl-3-methoxy-9H-imidazo[1,5-a][1,2,4]triazolo[1,5-d][1,4]benzodiazepine,
3-chloro-10-propyl-9H-imidazo[1,5-a][1,2,4]triazolo[1,5-d][1,4]benzodiazepine,
3-bromo-10-propyl-9H-imidazo[1,5-a][1,2,4]triazolo[1,5-d][1,4]benzodiazepine,
3-iodo-10-methyl-9H-imidazo[1,5-a][1,2,4]triazolo[1,5-d][1,4]benzodiazepine,
4-chloro-3-fluoro-10-methyl-9H-imidazo[1,5-a][1,2,4]triazolo[1,5-d][1,4]benzodiazepine,
4-fluoro-10-methyl-9H-imidazo[1,5-a][1,2,4]triazolo[1,5-d][1,4]benzodiazepine and
4-chloro-10-methyl-9H-imidazo[1,5-a][1,2,4]triazolo[1,5-d][1,4]benzodiazepine.

4. A compound of formula I in accordance with claim 1, wherein R$^3$ is —(CH$_2$)$_n$-cycloalkyl.

5. A compound of formula I in accordance with claim 4, which is 3-chloro-10-cyclopropylmethyl-9H-imidazo[1,5-a][1,2,4]triazolo[1,5-d][1,4]benzodiazepine.

6. A compound of formula I in accordance with claim 1, wherein R$^3$ is lower alkenyl.

7. A compound of formula I in accordance with claim 6, selected from the group consisting of 10-vinyl-9H-imidazo[1,5-a][1,2,4]triazolo[1,5-d][1,4]benzodiazepine,
3-fluoro-10-vinyl-9H-imidazo[1,5-a][1,2,4]triazolo[1,5-d][1,4]benzodiazepine,
3-chloro-10-vinyl-9H-imidazo[1,5-a][1,2,4]triazolo[1,5-d][1,4]benzodiazepine,
3-chloro-10-(E)-propenyl-9H-imidazo[1,5-a][1,2,4]triazolo[1,5-d][1,4]benzodiazepine and
3-chloro-10-(Z)-propenyl-9H-imidazo[1,5-a][1,2,4]triazolo[1,5-d][1,4]benzodiazepine.

8. A compound of formula I in accordance with claim 1, wherein R$^3$ is lower alkenyl-cycloalkyl.

9. A compound of formula I in accordance with claim 8, selected from the group consisting of 3-chloro-10-((E)-2-cyclopropyl-vinyl)-9H-imidazo[1,5-a][1,2,4]triazolo[1,5-d][1,4]benzodiazepine and
3-chloro-10-((Z)-2-cyclopropyl-vinyl)-9H-imidazo[1,5-a][1,2,4]triazolo[1,5-d][1,4]benzodiazepine.

10. A compound of formula I in accordance with claim 1, wherein R$^3$ is lower alkynyl.

11. A compound of formula I in accordance with claim 10, selected from the group consisting of 10-ethynyl-3-fluoro-9H-imidazo[1,5-a][1,2,4]triazolo[1,5-d][1,4]benzodiazepine,
3-chloro-10-ethynyl-9H-imidazo[1,5-a][1,2,4]triazolo[1,5-d][1,4]benzodiazepine and
3-bromo-10-ethynyl-9H-imidazo[1,5-a][1,2,4]triazolo[1,5-d][1,4]benzodiazepine.

12. A compound of formula I in accordance with claim 1, wherein R$^3$ is optionally substituted lower alkynyl-phenyl.

13. A compound of formula I in accordance with claim 12, selected from the group consisting of 3-fluoro-10-phenylethynyl-9H-imidazo[1,5-a][1,2,4]triazolo[1,5-d][1,4]benzodiazepine,
3-chloro-10-phenylethynyl-9H-imidazo[1,5-a][1,2,4]triazolo[1,5-d][1,4]benzodiazepine,
3-fluoro-10-(3-fluoro-phenylethynyl)-9H-imidazo[1,5-a][1,2,4]triazolo[1,5-d][1,4]benzodiazepine,
3-fluoro-10-(3-chloro-phenylethynyl)-9H-imidazo[1,5-a][1,2,4]triazolo[1,5-d][1,4]benzodiazepine,
3-fluoro-10-(3-trifluoromethyl-phenylethynyl)-9H-imidazo[1,5-a][1,2,4]triazolo[1,5-d][1,4]benzodiazepine,
3-fluoro-10-(3-methoxy-phenylethynyl)-9H-imidazo[1,5-a][1,2,4]triazolo[1,5-d][1,4]benzodiazepine,
3-fluoro-10-(3-methyl-phenylethynyl)-9H-imidazo[1,5-a][1,2,4]triazolo[1,5-d][1,4]benzodiazepine and
3-fluoro-10-(3-isopropyl-phenylethynyl)-9H-imidazo[1,5-a][1,2,4]triazolo[1,5-d][1,4]benzodiazepine.

14. A compound of formula I in accordance with claim 1, wherein R$^3$ is lower alkynyl-(CR'R")$_m$OH.

15. A compound of formula I in accordance with claim 14, which is 3-chloro-10-(3-hydroxy-3-methyl-but-1-ynyl)-9H-imidazo[1,5-a][1,2,4]triazolo[1,5-d][1,4]benzodiazepine.

16. A compound of formula I in accordance with claim 1, wherein R$^3$ is lower alkenyl substituted by halogen or is lower alkyl substituted by halogen.

17. A compound of formula I in accordance with claim 16, selected from the group consisting of 10-(2,2-difluoro-vinyl)-9H-imidazo[1,5-a][1,2,4]triazolo[1,5-d][1,4]benzodiazepine and
10-(2,2-difluoro-ethyl)-9H-imidazo[1,5-a][1,2,4]triazolo[1,5-d][1,4]benzodiazepine.

18. A compound of formula I in accordance with claim 1, wherein R$^2$ is hydrogen.

19. A compound of formula I in accordance with claim 1, wherein R$^2$ is methyl.

20. A compound of formula I in accordance with claim 1, wherein R$^1$ is lower alkyl, lower alkyl substituted by halogen, or cycloalkyl.

21. A compound of formula I in accordance with claim 1, wherein R$^1$ is lower alkoxy, lower alkoxy substituted by halogen, or —O(CH$_2$)$_m$O(CH$_2$)$_m$OH.

22. A compound of formula I in accordance with claim 1, wherein R$^1$ is hydrogen, halogen, nitro, or —C≡C—R'.

23. A pharmaceutical composition comprising a therapeutically effective amount of a compound of formula I

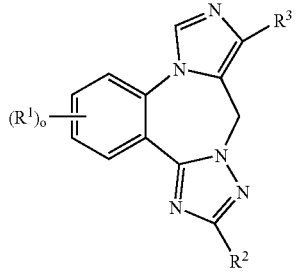

wherein
- $R^1$ is hydrogen, halogen, lower alkyl, lower alkyl substituted by halogen, lower alkoxy, lower alkoxy substituted by halogen, nitro, cycloalkyl, —O(CH$_2$)$_m$O(CH$_2$)$_m$OH or —C≡C—R';
- $R^2$ is hydrogen or methyl;
- $R^3$ is lower alkyl, lower alkyl substituted by halogen, lower alkenyl, lower alkenyl substituted by halogen, lower alkynyl, —(CH$_2$)$_n$-cycloalkyl, —(CR'R")$_m$—CH$_3$, phenyl that is unsubstituted or substituted by halogen, pyridinyl or thienyl each of which is unsubstituted or substituted by lower alkyl, —(CH$_2$)$_n$—NH-cycloalkyl, lower alkenyl-cycloalkyl, lower alkynyl-(CR'R")$_m$OH, or lower alkynyl-phenyl wherein the phenyl ring is unsubstituited or substituted by halogen, CF$_3$, lower alkyl or lower alkoxy;
- R' is hydrogen or lower alkyl;
- R" is hydrogen, hydroxy or lower alkyl;
- n is 0, 1 or 2;
- m is 1, 2 or 3; and
- o is 1 or 2;

or a pharmaceutically acceptable acid addition salt thereof and a pharmaceutically acceptable carrier.

24. A method of treating Alzhemier's disease or enhancing cognition comprising administering to an individual a therapeutically effective amount of a compound of formula I

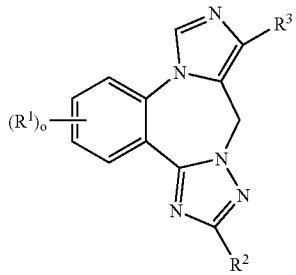

wherein
- $R^1$ is hydrogen, halogen, lower alkyl, lower alkyl substituted by halogen, lower alkoxy, lower alkoxy substituted by halogen, nitro, cycloalkyl, —O(CH$_2$)$_m$O(CH$_2$)$_m$OH or —C≡C—R';
- $R^2$ is hydrogen or methyl;
- $R^3$ is lower alkyl, lower alkyl substituted by halogen, lower alkenyl, lower alkenyl substituted by halogen, lower alkynyl, —(CH$_2$)$_n$-cycloalkyl, —(CR'R")$_m$—CH$_3$, phenyl that is unsubstituted or substituted by halogen, pyridinyl or thienyl each of which is unsubstituted or substituted by lower alkyl, —(CH$_2$)$_n$—NH-cycloalkyl, lower alkenyl-cycloalkyl, lower alkynyl-(CR'R")$_m$OH, or lower alkynyl-phenyl wherein the phenyl ring is unsubstituited or substituted by halogen, CF$_3$, lower alkyl or lower alkoxy;
- R' is hydrogen or lower alkyl;
- R" is hydrogen, hydroxy or lower alkyl;
- n is 0, 1 or 2;
- m is 1, 2 or 3; and
- 0 is 1 or 2;

or a pharmaceutically acceptable acid addition salt thereof.

* * * * *